(12) United States Patent
Gray et al.

(10) Patent No.: US 7,255,690 B2
(45) Date of Patent: Aug. 14, 2007

(54) INFUSION DEVICE HAVING PISTON OPERATED DRIVING MECHANISM AND POSITIVE PRESSURE RESERVOIR

(75) Inventors: John Gray, Woodland Hills, CA (US); Robert W. Bosley, Cerritos, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 400 days.

(21) Appl. No.: 10/331,187

(22) Filed: Dec. 26, 2002

(65) Prior Publication Data

US 2004/0127852 A1  Jul. 1, 2004

(51) Int. Cl.
*A61M 1/00* (2006.01)
*A61K 9/22* (2006.01)

(52) U.S. Cl. .................... 604/891.1; 604/152

(58) Field of Classification Search ............ 604/65–67, 604/890.1, 891.1, 288, 171, 192, 152, 158, 604/892.1, 131, 141, 151, 154, 93.01, 99.04; 417/53, 44.1, 44.7, 415–418
See application file for complete search history.

(56) References Cited

U.S. PATENT DOCUMENTS

| | | | |
|---|---|---|---|
| 4,193,397 A | 3/1980 | Tucker et al. | |
| 4,360,019 A * | 11/1982 | Portner et al. | 604/131 |
| 4,373,527 A | 2/1983 | Fischell | |
| 4,437,815 A | 3/1984 | McMullen | |
| 4,468,221 A | 8/1984 | Mayfield | |
| 4,568,250 A | 2/1986 | Falk et al. | |
| 4,569,641 A | 2/1986 | Falk et al. | |
| 4,573,994 A | 3/1986 | Fischell et al. | |
| 4,576,556 A | 3/1986 | Thompson | |
| 4,594,058 A | 6/1986 | Fischell | |
| 4,636,150 A | 1/1987 | Falk et al. | |
| 4,684,368 A * | 8/1987 | Kenyon | 604/152 |
| 4,692,147 A | 9/1987 | Duggan | |
| 4,697,622 A | 10/1987 | Swift et al. | |
| 4,714,234 A | 12/1987 | Falk et al. | |

(Continued)

FOREIGN PATENT DOCUMENTS

WO  WO 03/022328 A2  3/2003

OTHER PUBLICATIONS

EP Search Report as issued in European Patent Application No. 03796554.8-2310, Mailing date: Feb. 14, 2006.

*Primary Examiner*—Matthew DeSanto
(74) *Attorney, Agent, or Firm*—Foley & Lardner LLP

(57) ABSTRACT

A piston-type drive mechanism in combination with a positive pressure reservoir for delivery of infusion medium. A coil capable of being electrically activated to provide an electromagnetic field. The coil surrounds a piston channel extending in an axial direction. The piston channel provides a passage for communication of infusion medium from the positive pressure reservoir to an outlet chamber. A piston is located within the piston channel and is moveable axially within the channel to a forward position. The piston is moved toward a retracted position, when the coil is not energized. As the piston is moved to its forward position, pressure moves a valve member into an open position. When the valve member is in the open position, medium from the piston chamber is discharged into the outlet chamber. An outlet is provided in flow communication with the outlet chamber, for discharging infusion medium from the outlet chamber.

26 Claims, 12 Drawing Sheets

U.S. PATENT DOCUMENTS

| | | | |
|---|---|---|---|
| 4,715,852 A * | 12/1987 | Reinicke et al. ............ 604/131 |
| 4,808,089 A | 2/1989 | Buchholtz et al. |
| 4,883,467 A | 11/1989 | Franetzki et al. |
| 4,985,015 A | 1/1991 | Obermann et al. |
| 5,167,633 A | 12/1992 | Mann et al. |
| 5,176,644 A | 1/1993 | Srisathapat et al. |
| 5,318,521 A | 6/1994 | Slettenmark |
| 4,373,527 A | 6/1995 | Fischell |
| 5,514,103 A | 5/1996 | Srisathapat et al. |
| 5,527,307 A | 6/1996 | Srisathapat et al. |
| 5,797,733 A | 8/1998 | Falk et al. |
| 6,193,477 B1 | 2/2001 | Falk et al. |
| 6,227,818 B1 | 5/2001 | Falk et al. |
| 6,264,432 B1 | 7/2001 | Kilayko et al. |
| 6,264,439 B1 | 7/2001 | Falk et al. |
| 2002/0173772 A1 * | 11/2002 | Olsen ...................... 604/891.1 |

* cited by examiner

INFUSION DEVICE HAVING PISTON OPERATED DRIVING MECHANISM AND POSITIVE PRESSURE RESERVOIR

FIELD OF THE INVENTION

The present invention relates generally to infusion devices and methods, in particular embodiments to implantable infusion devices and methods employing in combination a positive pressure reservoir and a piston-type driving mechanism functioning as a metering valve.

RELATED ART

Infusion devices, including implantable infusion devices, are frequently used for delivering drugs or other liquid medications over long periods of time to selected locations in the human body. These devices commonly include a drug reservoir having a catheter port and catheter means connected to the catheter port to transport the drug from the reservoir to a patient's anatomy by means of a drive mechanism. The drive mechanism propels the drug in some metered or constant flow dosage to the desired infusion site. Such devices also typically include a battery to power the drive mechanism as well as an electronic module to control the flow rate of the drive mechanism.

A peristaltic pump or "roller pump" is commonly used as the drive mechanism to deliver a drug into a patient's system. Peristaltic or roller pumps typically incorporate coplanar geometry in which pump rollers orbit within the plane defined by a pump tube, which is held in a stationary race. Exemplary peristaltic pumps are disclosed in commonly assigned U.S. Pat. No. 4,692,147 (Duggan) and U.S. Pat. No. 4,576,556 (Thompson). It has been demonstrated that peristaltic pumps such as those described in the Thompson '556 and Duggan '147 patents provide a highly reliable mechanism for inclusion in a totally body-implantable drug infusion pump including a control system, power source, fluid reservoir, and refilling mechanism.

A roller pump generally operates to pump liquid and/or compressible gas mixtures, for example, by repeatedly squeezing a flexible tube to push the pumped substance through the tube. Typically, roller pumps employ a stator having a bearing surface against which one or more flexible tubes or hoses is compressed by a rotating rotor, the rotor engaging the hoses with two or more rollers, thus providing the flexible tubes with advancing occluded portions, causing fluid to be pumped from one location to another through the tubes. On rotation of the rotor, the fluid in the tube or tubes is transported in the direction of the rotor's rotation.

Alternatively, the fluid can be presented to the pump under positive pressure, such that rotation of the rotor causes the pump to serve as a measuring or "metering" valve. In this instance, the infusion device may incorporate a positive pressure reservoir. The positive pressure reservoir may be provided with a pressurizing means such that the contents of the reservoir are continuously pressurized and are metered through the drive mechanism and through the tube or tubes in response to, for example, an actuation signal. The pressurizing means may simply be a spring loaded actuator acting on a flexible bag type reservoir or may incorporate pressurized gas or a resilient bag to constantly maintain the contents of the reservoir under pressure. Knowledge as to the inner diameter of the tube or tubes and the rotational speed of the rotor provides an indication of the amount of fluid metered through the tube or tubes, which amount can be regulated by regulating the speed of the rotor.

One problem associated with roller pumps is that they typically require a great deal of effort and expense in their assembly and maintenance in order to closely control the tolerances relating to the tube alignment and the occluding force applied by the rollers to various portions of the tube. In addition, mechanical wear of elastomeric tubes resulting from the roller action involves increased maintenance requirements.

An additional problem associated with roller pumps is that mechanical friction produced by passing the roller or rollers over a fluid-swollen tube surface creates a large energy requirement, which can further limit the pump's functional longevity. As was stated above, infusion devices such as roller pumps typically include a battery to power the drive mechanism. It is important that the drive mechanism consume as little electrical energy as possible for the quantity of fluid which it is to handle. This is important for at least two reasons. First, the less electrical energy the drive mechanism consumes, the smaller may be the battery or batteries within the infusion devices, thereby enabling the infusion devices to be made smaller than might otherwise be the case. Second, in the case of implanted infusion devices, the less electrical energy the drive mechanism consumes, the longer any particular size of battery will last, thereby avoiding frequent surgical replacement of the infusion device or its batteries.

Another type of drive mechanism employs electromagnetic and mechanical forces to move a piston between retracted and forward positions or states, to cause infusion medium to be drawn from a negative pressure reservoir, through an inlet and forced out of an outlet. An exemplary drive mechanism of this type is disclosed in commonly assigned U.S. patent application Ser. No. 10/033,722, titled "Infusion Device And Driving Mechanism For Same", filed Dec. 27, 2001, which is incorporated herein by reference.

The drive mechanism includes a coil disposed within a coil cup, a piston channel surrounded by the coil, a piston extending through the piston channel, an armature disposed at one end of the piston channel and an outlet chamber with a valve assembly disposed at the other end of the piston channel.

When the coil is in a quiescent state, the armature and piston are urged toward a retracted position by mechanical or magnetic forces. When the coil is energized, the armature and piston move to a forward stroke position. The movement of the piston from a retracted position to a forward position creates pressure differentials within the drive mechanism to drive medium out the outlet. Mechanical force may return the piston to the retracted position. The movement of the piston from a forward position to a retracted position creates pressure differentials to draw medium into an inlet of the drive mechanism from the negative pressure reservoir.

Because a negative pressure reservoir is used with this type of drive mechanism rather than a positive pressure reservoir, the medium must be drawn out of the reservoir and into the drive mechanism in order to prime the drive mechanism. This requires that the drive mechanism include features for drawing the medium from the negative pressure reservoir and through a flow path to the outlet chamber rather than receiving the medium via positive pressure. This may require increased design, manufacturing and assembly costs for the drive mechanism.

Thus, there is a demand in the industry for infusion devices that operate in combination with a positive pressure reservoir which avoid the effort and expense required in closely controlling the tolerances relating to tube alignment and roller occluding force on the tubes. There is also a demand in the industry for infusion devices that operate in combination with a positive pressure reservoir which make efficient use of electrical energy and may be designed, manufactured, assembled and maintained at reduced costs.

SUMMARY OF THE DISCLOSURE

Accordingly, embodiments of the present invention relate to infusion devices which address the above-mentioned industry demands.

Preferred embodiments of the invention relate to such devices and drive mechanisms configured for implantation in a patient's body. Configurations described herein allow the drive mechanism to be designed, manufactured, assembled and maintained at reduced costs.

Further preferred embodiments relate to such devices and drive mechanisms configured and operated to make highly efficient use of electrical power to prolong operational life.

Yet further preferred embodiments relate to such devices and drive mechanisms configured to deliver relatively precisely controlled volumes of infusion medium, within a relatively wide range of volumes, including relatively small volumes.

Yet further preferred embodiments relate to such devices and drive mechanisms configured to deliver sufficiently precise volumes of relatively high concentration infusion medium.

An infusion device according to an embodiment of the invention includes a generally disc-shaped housing made from a biocompatible and infusion medium compatible material. The infusion device housing contains a positive pressure reservoir for holding a volume of infusion medium under positive pressure, such as, but not limited to, a medication to be administered to the patient. The infusion device housing has an outlet through which the infusion medium may be expelled.

The infusion device further includes a drive mechanism having an inlet coupled in fluid flow communication with the positive pressure reservoir and an outlet coupled in fluid flow communication with the infusion device housing outlet. In one embodiment, a filter may be disposed between the reservoir and the drive mechanism (or as part of the inlet of the drive mechanism). In a further embodiment, expandable and compressible devices, such as one or more volume compensators or accumulators, which may also be, for example, accumulators, also may be disposed in the flow path between the positive pressure reservoir and the drive mechanism inlet, to dampen surges and ebbs in the flow.

The drive mechanism employs electromagnetic and mechanical forces to move a piston between retracted and forward positions or states to cause infusion medium provided to the drive mechanism by the positive pressure reservoir to be forced out of an outlet. A drive mechanism, according to one embodiment, comprises an assembly of components which may be manufactured and assembled in a relatively cost efficient manner. The components include a housing containing a coil disposed within a coil cup, a piston channel surrounded by the coil, a piston extending through the piston channel, an armature disposed at one end of the piston channel and an outlet chamber with a valve assembly disposed at the other end of the piston channel.

When the coil is in a quiescent state, the armature and piston are urged toward a retracted position by mechanical or magnetic forces. When the coil is energized, the armature and piston move to a forward stroke position. The movement of the piston from a retracted position to a forward position creates pressure differentials within the drive mechanism to drive medium out the outlet. Mechanical force may return the piston to the retracted position.

Further embodiments may include an outlet port and one or more fluid flow damping or accumulator structures, such as pillows or accumulators in pillow or accumulator cavities, in the housing, to help provide a relatively stable, constant output pressure during drive operations. The accumulator cavities, outlet port and outlet chamber may share a common portion of the thickness dimension of the drive mechanism, to maintain a relatively thin form factor.

Further embodiments may include a check valve to open and close the fluid flow path between the outlet chamber and the infusion site to provide additional protection against unwanted discharge of infusion medium from the infusion device. In preferred embodiments, the additional check valve may be located within the outlet chamber. However, in other embodiments, the check valve may be located elsewhere in the flow path between the outlet chamber and an infusion site, including within the outlet port, within a catheter attached between the outlet port and the infusion site or in any other suitable location.

Yet further embodiments may include additionally, or in the alternative, a conventional pressure regulating valve in the medium flow path. The pressure at which medium flows through the flow path is may be sensed by the pressure regulating valve. In one embodiment, the pressure regulating valve may have a low pressure cut-off point approximately equal to the pressure exerted by the positive pressure reservoir on the medium. Any medium flowing at a pressure below this low pressure cut-off point will be blocked by the pressure regulating valve. In this manner, any undesired leakage of the medium may be minimized.

Still further embodiments may include a bacterial particulate filter may be included in the flow path of the infusion medium for trapping particulate matter in the infusion medium.

These and other aspects and advantages of the invention will be apparent to one of skill in the art from the accompanying detailed description and drawings.

BRIEF DESCRIPTION OF THE DRAWINGS

Referring now to the drawings in which like reference numbers represent corresponding parts throughout.

DETAILED DESCRIPTION OF PREFERRED EMBODIMENTS

Figure 1:
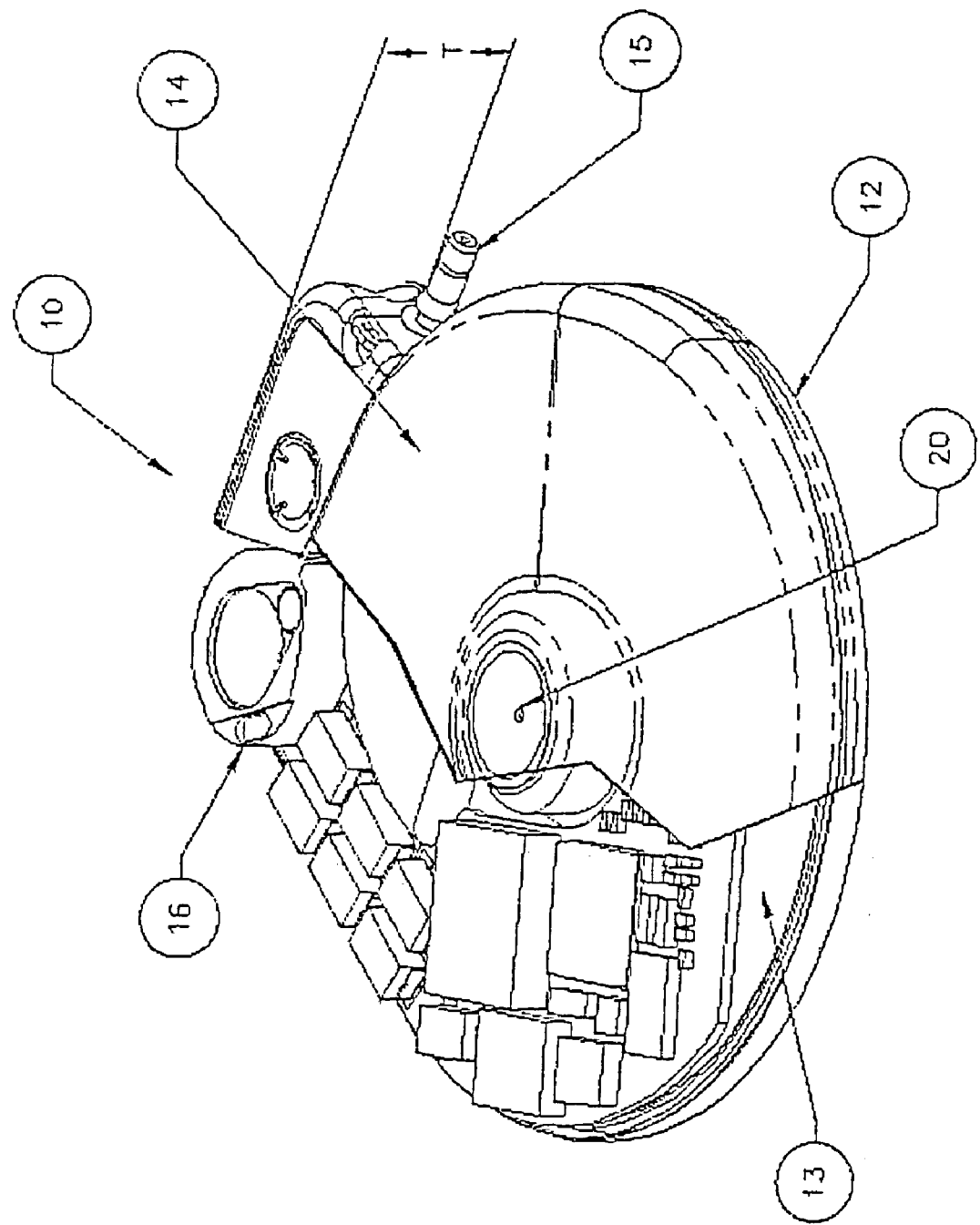
FIG. 1 is a perspective view of an implantable infusion device according to an embodiment of the invention.

The following detailed description is of the best presently contemplated mode of implementing the invention. This description is not to be taken in a limiting sense, but is made merely for the purpose of illustrating the general principles of embodiments of the invention. The scope of the invention is best defined by the appended claims.

As discussed above, the present invention relates generally to infusion devices and methods and, in particular embodiments to implantable infusion devices and methods employing in combination a positive pressure reservoir and a piston-type driving mechanism functioning as a metering valve. Preferred embodiments of the invention relate to such devices and systems configured for implantation in a patient's body. Configurations described herein allow the infusion device to include a piston-type drive mechanism in combination with a positive pressure reservoir which avoids the effort and expense required in closely controlling tolerances relating to tube alignment and roller occluding force on the tubes that is required for peristaltic drive mechanisms. Configurations described herein also allow more efficient use of electrical power and increased functional longevity by avoiding the consumption of electrical power associated with mechanical friction produced by passing a roller or rollers over a tube surface in peristaltic or roller pumps.

Preferred embodiments of the invention relate to infusion devices and drive mechanisms configured for implantation in a patient's body. Further preferred embodiments employ power consumption efficiency aspects and features referenced above to provide improved operational life within an implant environment. Yet further preferred embodiments relate to such devices and drive mechanisms configured to deliver relatively precisely controlled volumes of infusion medium, within a relatively wide range of volumes, including relatively small volumes. Yet further preferred embodiments relate to such devices and drive mechanisms configured to deliver sufficiently precise volumes of relatively high concentration infusion medium.

An infusion device according to an embodiment of the invention includes a generally disc-shaped housing made from a biocompatible material. The housing contains a reservoir for holding a volume of infusion medium, such as, but not limited to, a medication to be administered to the patient. The housing has an outlet through which the infusion medium may be expelled. The reservoir is coupled in fluid flow communication with the outlet. The infusion device also includes or operates with a drive mechanism coupled in fluid flow communication with the reservoir. The infusion device further includes or operates with an electronic power control system for controlling and providing electronic power to the drive mechanism. A drive mechanism, according to preferred embodiments, employs electromagnetic and mechanical forces to move between retracted (or quiescent) and forward states, to cause infusion medium, provided to the drive mechanism under positive pressure from a positive pressure reservoir, to be forced out of an outlet of the drive mechanism.

A preferred pump configuration includes a housing containing an electrical coil disposed within a core or coil cup made of magnetizable material, a piston extending through an axial channel in the coil and coil cup, an armature disposed at one end of the axial channel and an outlet chamber with a valve assembly disposed at the other end of the axial channel. Other suitable pump configurations may be employed in other embodiments. In the quiescent state, the piston and armature are urged toward a retracted position. When the coil is energized, an electromagnetic field generated by the coil draws the armature toward the coil cup. As a result, the armature and piston move to a forward stroke position. The movement of the piston between retracted and forward positions creates pressure differentials within the internal chambers and volumes of the pump device, to drive medium out the outlet. A power control system, according to preferred embodiments of the invention, is configured for highly efficient use of electrical power by the drive mechanism.

FIG. 1 shows an implantable infusion device 10 according to an embodiment of the invention. The illustrated device 10 is configured to be surgically implanted into a patient, for example, in the abdominal region, between the skin and the abdominal wall. A catheter connected to the pump may deliver infusion medium to the patient, for example, by feeding infusion medium to a particular location in the venous system, within the spinal column or in the peritoneal cavity of the patient. As described below, preferred embodiments of the device 10 are configured in accordance with one or more aspects of the invention for enhancing implantability and prolonged usage once implanted. However, further embodiments of the invention may be implemented as external infusion devices, which connect to patients through suitable catheter devices or the like. Yet further embodiments of the invention may be used in other contexts, for delivery of a medium into other suitable environments. Therefore, for purposes of simplifying the present disclosure, the term "patient" is used herein to refer to the entity or environment in which an implantable device is implanted or to which an external device is connected, whether or not the implant or connection is carried out for medical purposes. Also, the term "infusion medium" is used herein to refer to any suitable medium delivered by the drive device.

The device 10 includes a generally disc-shaped housing 12. While a generally circular disc-shaped embodiment is illustrated in FIG. 1, it will be understood that further embodiments of the invention may employ housings of other shapes, including, but not limited to, oval, oblong, rectangular, or other curved or polygonal shapes. The housing 12 has a diameter dimension D, defining the diameter of the disc shape, and a maximum thickness dimension T, defining the maximum thickness of the device. In implantable device embodiments, the housing 12 is made of a biocompatible material and preferably has a relatively small or minimized thickness dimension T, to reduce or minimize patient trauma during implant surgery and after implantation.

The housing 12 includes a reservoir housing portion 13 containing a positive pressure reservoir for holding a volume of infusion medium, such as, but not limited to, a liquid medication to be administered to the patient. The housing 12 includes a further housing portion 14, located above the reservoir housing portion 13 in the orientation shown in FIG.

1, for containing a drive mechanism, a power source and control electronics described below.

Representative examples of reservoir housing portions and reservoirs which may be employed in embodiments of the invention are described in co-pending U.S. patent application Ser. No. 10/033,377, titled Implantable Infusion Device And Reservoir For Same, which is incorporated herein by reference. However, further embodiments may employ other suitable reservoir configurations, including, but not limited to, those described in U.S. Pat. No. 5,514,103 and U.S. Pat. No. 5,176,644, each to Srisathapat et al and U.S. Pat. No. 5,167,633 to Mann et al. In particular embodiments described herein, the reservoir contains (or is capable of containing) an infusion medium under a positive pressure. Positive pressure may be provided by employing gas or fluid propellant within the reservoir, for example, separated from the infusion medium by a suitable diaphragm, bellows or similar structure, for example, as described in pending U.S. patent application Ser. No. 10/033,377, cited above.

The housing 12 also has an outlet 16 through which the infusion medium may be expelled. When the device 10 is implanted in a patient or connected externally to a patient, a catheter may be connected to the outlet 16, to deliver infusion medium expelled from the outlet 16 into the patient's blood stream or to a selected location in the patient's body. The infusion device 10 also includes an inlet structure 15 which provides a closeable and sealable fluid flow path to the reservoir in the reservoir portion 13 of the housing. The inlet structure provides a port for receiving a needle through which fluid may be transferred to the infusion device, for example, to fill or re-fill the reservoir of the device. In preferred embodiments, the inlet structure is configured to re-seal after a fill or re-fill operation, and to allow multiple re-fill and re-seal operations. One example of an inlet structure is described in co-pending U.S. patent application Ser. No. 60/318,056, titled "Infusion Device And Inlet For Same," which is incorporated herein by reference. However, further embodiments may employ other suitable inlet structures, including, but not limited to, those described in U.S. Pat. No. 5,514,103 and U.S. Pat. No. 5,176,644, each to Srisathapat et al, U.S. Pat. No. 5,167,633 to Mann et al., U.S. Pat. No. 4,697,622 to Swift and U.S. Pat. No. 4,573,994 to Fischell et al.

The infusion device 10 includes a drive mechanism 20, such as a pump, and an electronic control system 22 located in the housing portion 14. The drive mechanism 20 is connected between the reservoir and the outlet 16. The electronic control system 22 includes a power source, such as a battery, and control electronics for controlling the drive mechanism 20 to deliver infusion medium from the reservoir, to the patient in a selected manner. The drive mechanism may be controlled to meter infusion medium in any suitable manner, for example, according to a programmed dispensing rate or schedule or according to an actuation signal from a sensor, timer or other suitable source.

In implantable embodiments, the portion 14 of the housing 12 that contains the drive mechanism 20 and control electronics 22 is preferably hermetically sealed from the external environment and from the reservoir housing portion 13. The housing portion 14 containing the drive mechanism 20 and control electronics 22 may be made from titanium or titanium alloy or other biocompatible metals.

The drive mechanism 20 includes mechanical and electromagnetic components that inherently inhabit a volume of space within the housing portion 14 in which the components reside and operate. In that regard, the drive mechanism 20 can contribute to the thickness requirements of the housing portion 14 and, thus, to the overall thickness dimension T of the device 10. Preferred embodiments of the present invention relate to and employ drive mechanism configurations that reduce or minimize the thickness requirements of the device, without compromising drive capabilities.

The ability to reduce or minimize the device thickness dimension T, without compromising the drive capabilities, can provide significant advantages with respect to patient comfort, appearance and flexibility in selecting implant locations in the body. Accordingly, drive mechanism configurations that allow for reduced or minimized device thickness dimensions, as described herein, can provide significant advantages in the implantable infusion device technology. Thus, in preferred embodiments, the drive mechanism 20 is configured with one or more features described herein that provide a relatively small or minimal thickness and allow the device 10 to have a relative small or minimal thickness T.

Also in preferred embodiments, the device 10 is configured such that, once implanted, it functions for a relatively long period of time to administer infusion medium to the patient and periodically be replenished from outside of the patient's body. The operational life of the device 10 is, however, limited in part by the capacity of its power source and the power requirements of the device. Preferred embodiments of the device 10 employ drive mechanisms, as described below, that provide reliable pumping or metering action and are highly efficient with respect to power consumption, to improve the operational life of the device 10. Alternatively or in addition, drive mechanisms that provide highly efficient use of power, as described below, may be operated with smaller power sources (for example, smaller batteries) which can allow the device 10 to be made smaller.

First Drive Mechanism Embodiment

Figure 2:
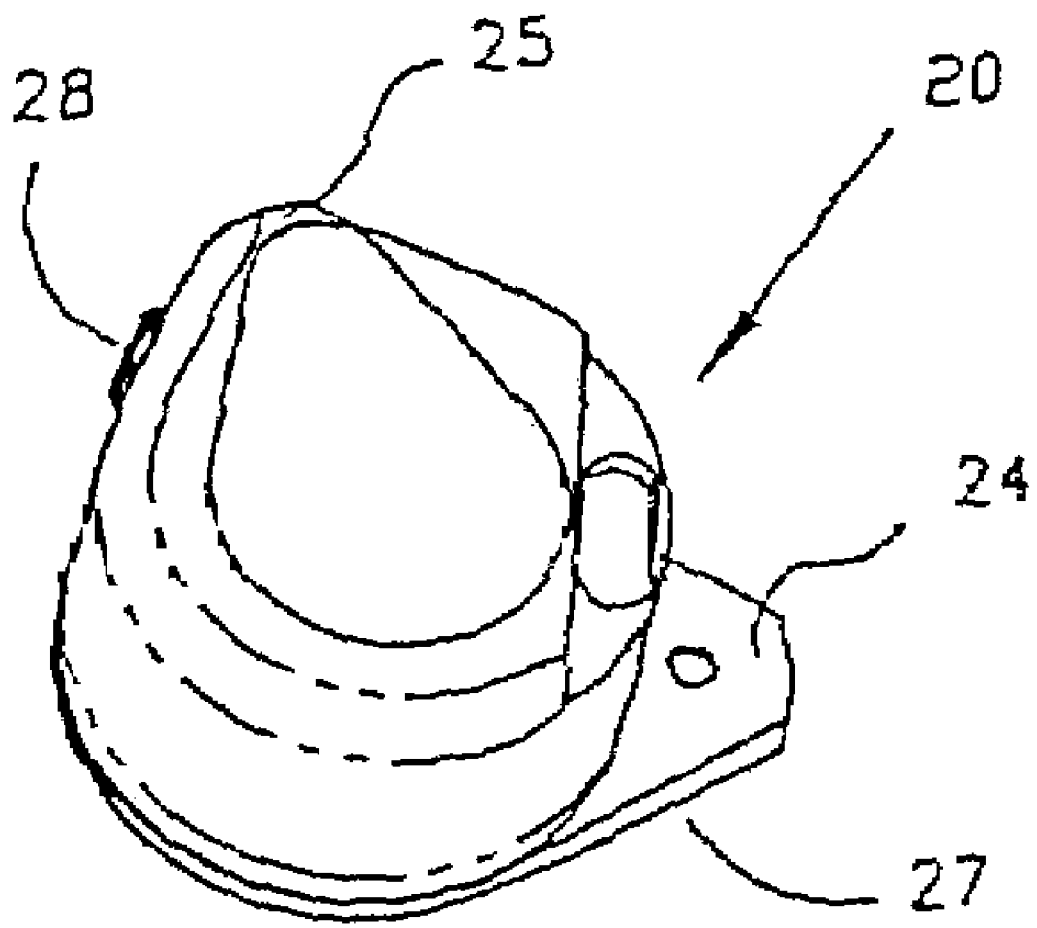
FIG. 2 is a perspective view of a drive mechanism for an implantable infusion device according to an embodiment of the invention.

FIG. 2 shows a drive mechanism 20 according to one example embodiment of the present invention. In the illustrated embodiment, the drive mechanism 20 has a partially cylindrical, disc-shaped configuration with extended corners 24 and 25. An inlet 27 is provided at the corner 24 and an outlet 28 is provided at the corner 25. The inlet 27 may be connected in flow communication with the reservoir portion 13 of the device 10 in FIG. 1, though suitable conduit (not shown) within the device 10. Similarly, the outlet 28 may be connected in flow communication with the outlet 16 of the device 10 in FIG. 1, through suitable conduit (not shown) within the device 10.

Figure 3:
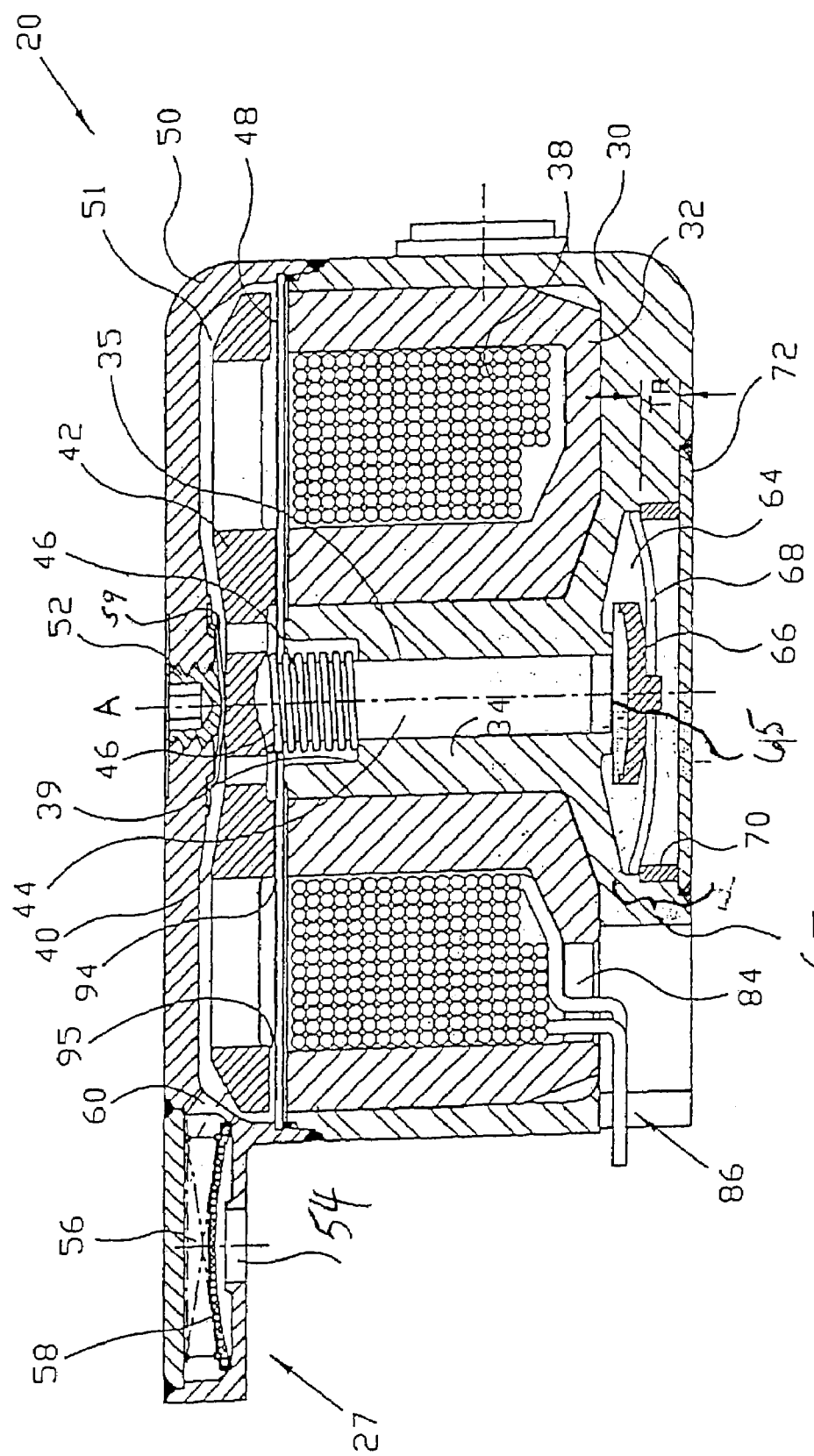
FIG. 3 is a cross-section view of one example embodiment of the drive mechanism of FIG. 2, in a retracted position or state.
Figure 4:
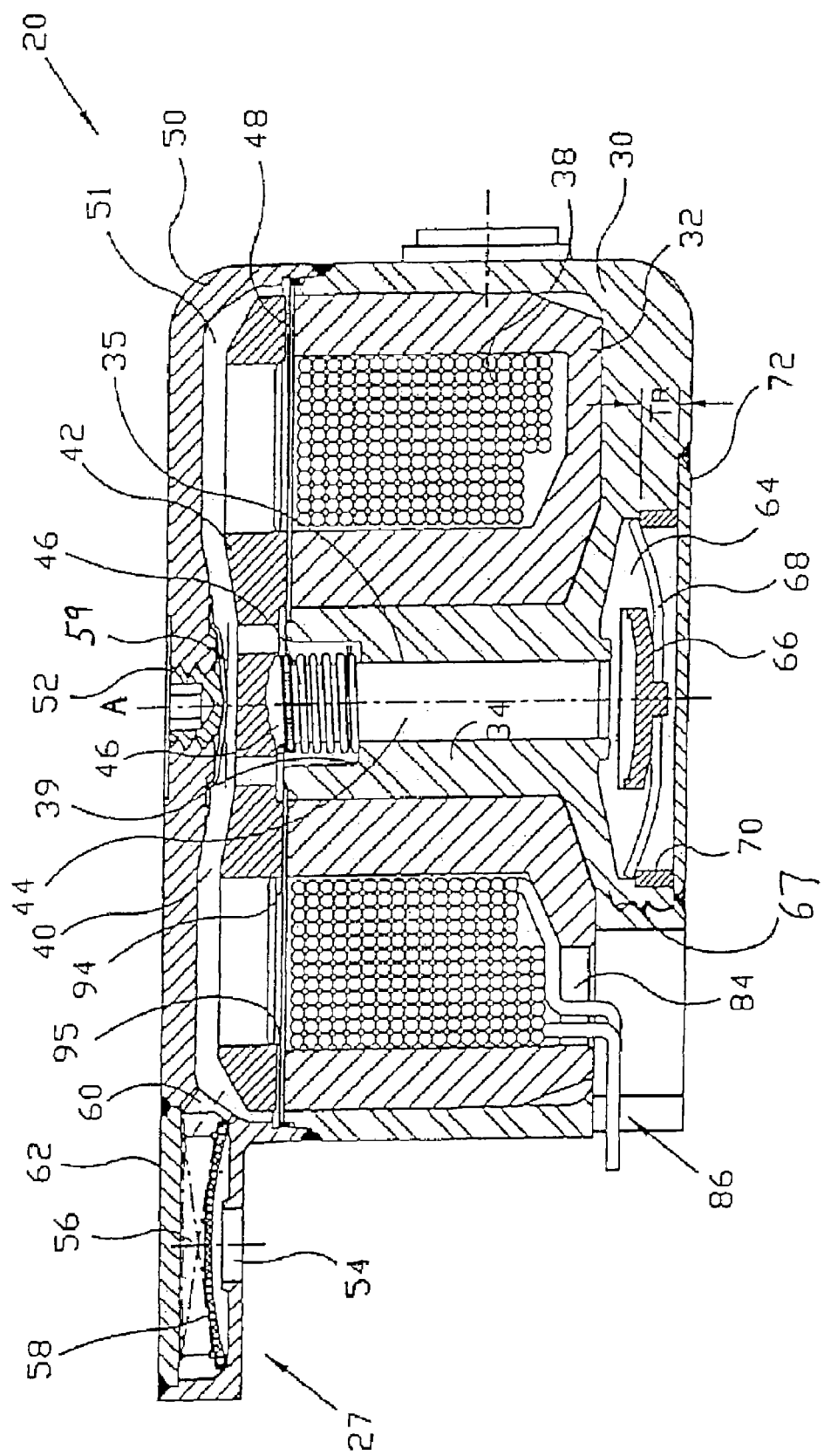
FIG. 4 is a cross-section view of the example drive mechanism embodiment of FIG. 3, in a forward stroke position or state.

FIG. 3 shows a cross-sectional view of an embodiment of a drive mechanism 20, in a retracted position or state. FIG. 4 shows a cross-sectional view of the same drive mechanism 20 embodiment, in a forward position or state. As described in more detail below, the drive mechanism 20 employs electromagnetic and mechanical forces to change (or move) between retracted and forward states, to cause infusion medium to be forced out of the outlet 28. The drive mechanism 20, according to one embodiment, comprises an assembly of components as shown in an exploded view in FIG. 5. Some of these components are also shown in perspective views in FIGS. 6-10.

Figure 6:
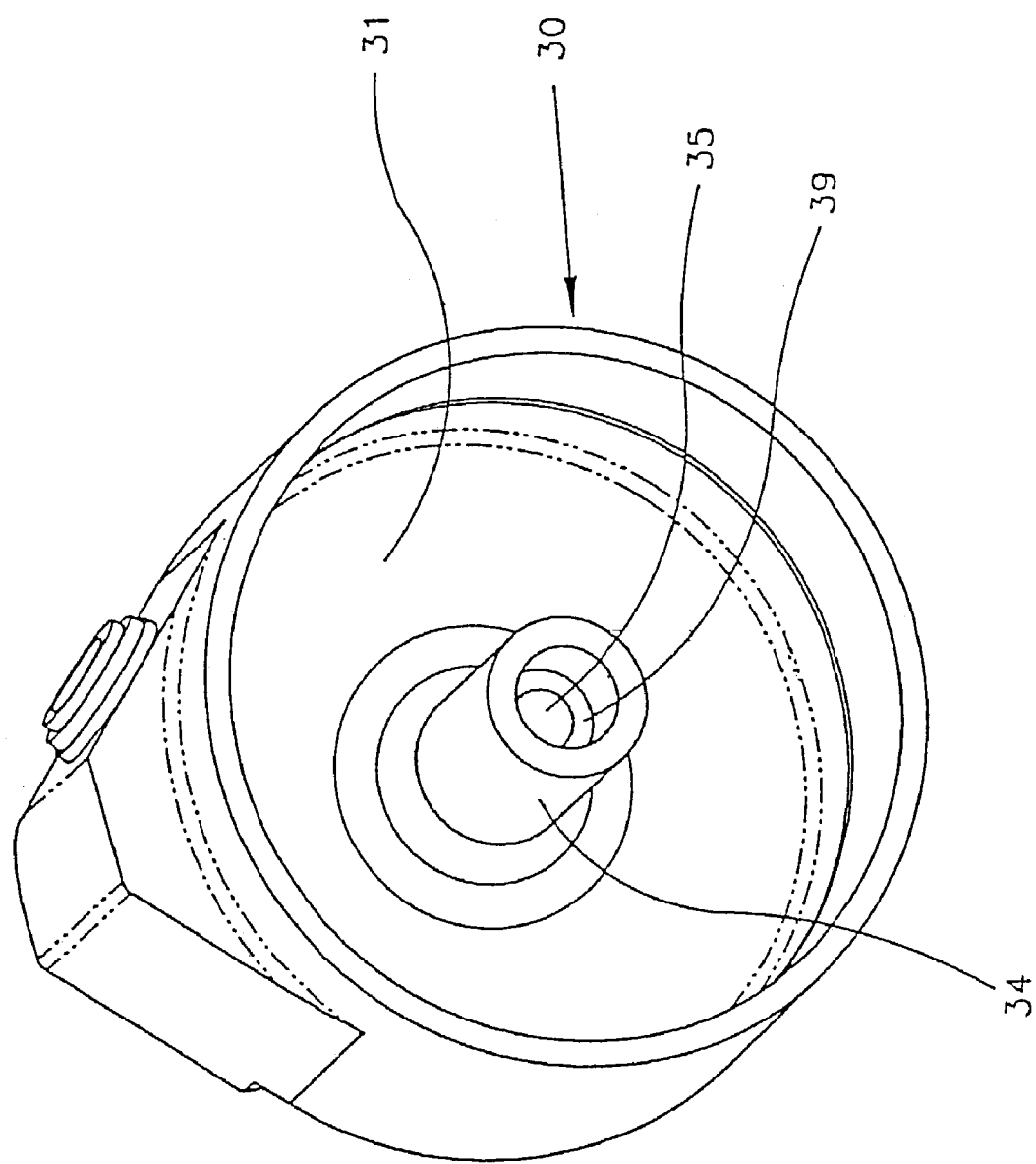
FIG. 6 is a perspective view of an embodiment of the inlet end of a housing for the drive mechanism in FIGS. 3 and 4.
Figure 7:
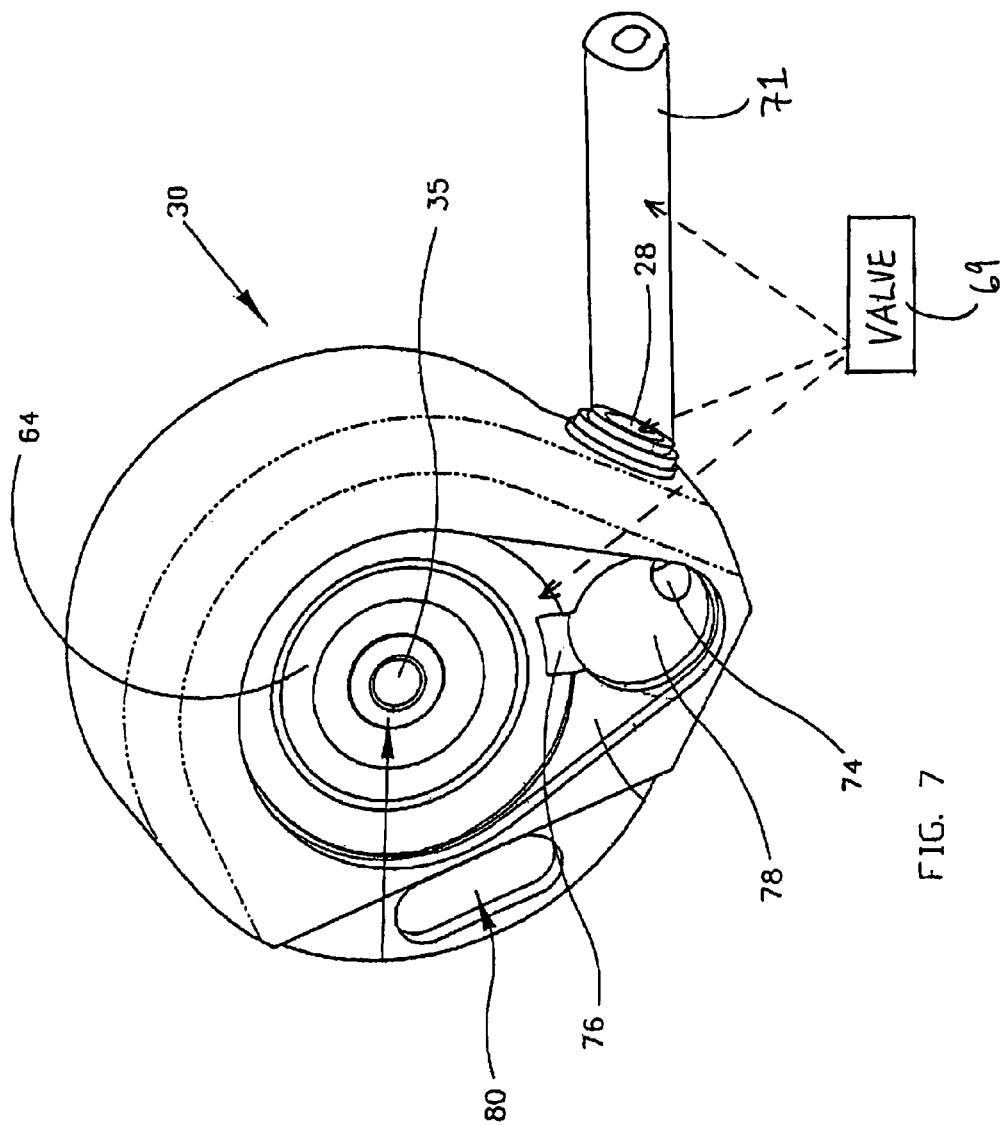
FIG. 7 is a perspective view of an embodiment of the outlet end of the drive mechanism housing of FIG. 6.

With reference to those drawings, the drive mechanism 20 includes a housing member 30 that is open on one side to a hollow, annular interior section 31. FIGS. 6 and 7 show two perspective views of the housing 30. The housing member 30 has a central hub portion 34 with a central piston channel 35. The bottom side of the housing member 30 (with reference to the orientation shown in FIGS. 3 and 4), includes an opening to the hollow interior section 31 through which coil wires may pass, as described below. The bottom side of the housing member also includes a configuration of recesses and cavities for providing an outlet chamber, an outlet passage and, in some embodiments, accumulator chambers as described below. The housing member 30 is preferably made of a generally rigid, biocompatible and infusion medium compatible material, having no or low magnetic permeability such as, but not limited to, titanium, stainless steel (which may be ferritic or non-ferritic), biocompatible plastic, ceramic, glass or the like.

Figure 8:
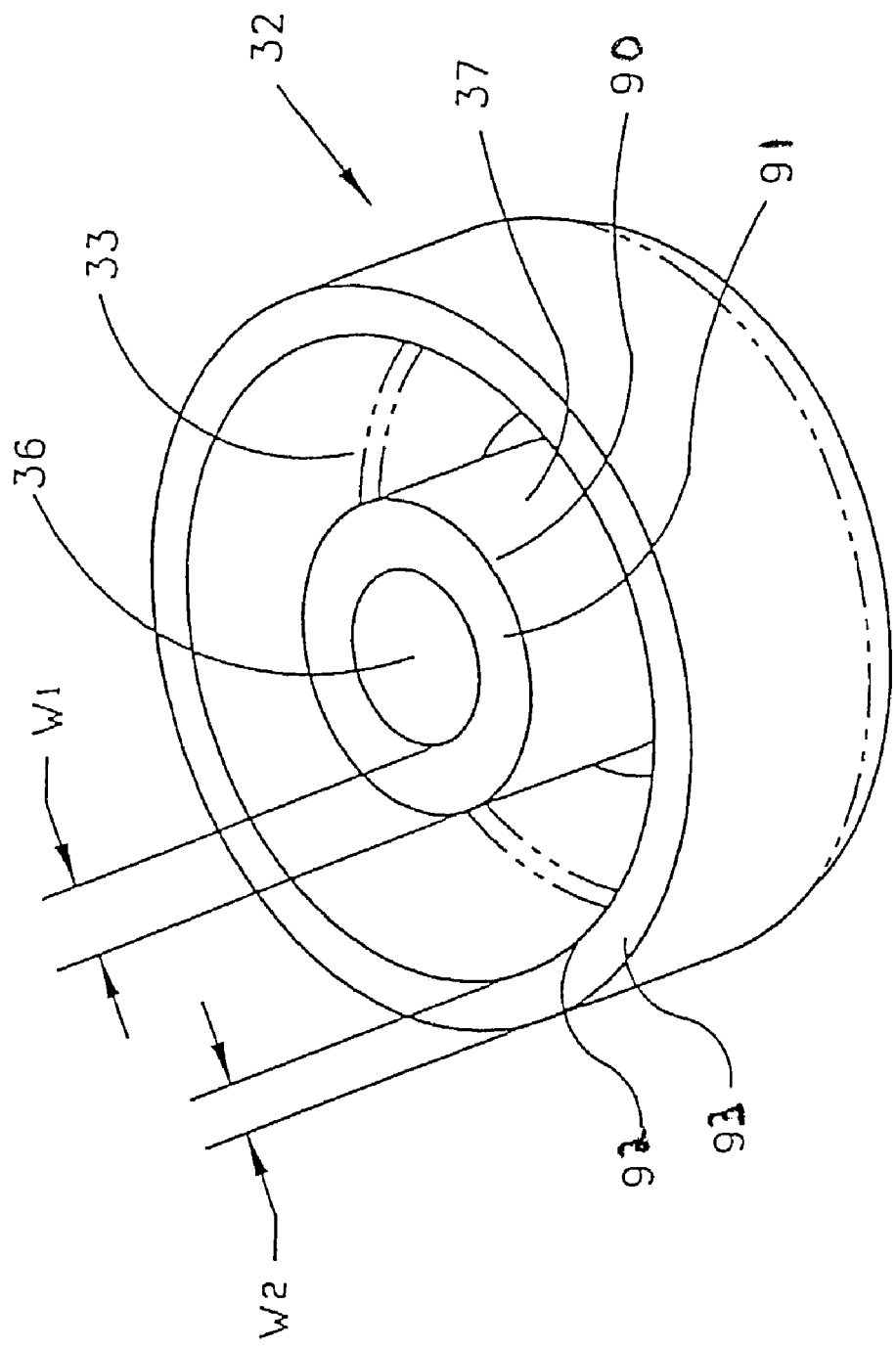
FIG. 8 is a perspective view of an embodiment of a coil cup for the drive mechanism in FIGS. 3 and 4.

As shown in FIGS. 3 and 4, a coil cup 32 is located within the annular interior section of the housing 30. A perspective view of the coil cup 32 is shown in FIG. 8. The coil cup 32 has a generally cylinder shape, open on one side to a hollow, annular interior 33. The coil cup includes an open piston channel or bore 36 located in a central hub portion 37, axial relative to the annular interior. The hub portion 37 of the cup member defines an inner annular wall 90 having an end surface 91 (or inner pole surface) of width $W_1$. The cup member has an outer wall 92 having an end surface 93 (or outer pole surface) of a width $W_2$. The outer wall 92 is connected to the inner wall 90 or hub portion 37 by a backiron portion of the cup member. As described in further detail below, at the open end of the cup member, the end surfaces 91 and 93 of the inner and outer walls 90 and 92 define pole surfaces that cooperate with pole surfaces on an armature to provide a path for electromagnetic flux during a forward stroke of the drive mechanism. In preferred embodiments, the width $W_1$ of inner pole surface 91 is greater than the width $W_2$ of the outer pole surface 93, to provide certain electromagnetic characteristics as described below.

When assembled, the coil cup is located in the hollow interior of the housing member 30, with the central portion 34 of the housing 30 extending through the piston channel 36 of the coil cup 32, as shown in FIGS. 3 and 4. A coil 38 is located within the hollow, annular interior of the coil cup 32, and is disposed around the axis A of the annular interior of the coil cup 32. The coil cup 32 is provided with an opening 84, through which coil leads extend, as shown in FIGS. 3 and 4. The coil cup 32 is preferably made of a generally rigid material, having a relatively high magnetic permeability such as, but not limited to, low carbon steel, iron, nickel, ferritic stainless steel, ferrite, other ferrous materials, or the like. The coil 38 comprises a conductive wire wound in a coil configuration. The coil wire may comprise any suitable conductive material such as, but not limited to, silver, copper, gold or the like, with each turn electrically insulated from adjacent turns and the housing. In one preferred embodiment, the coil wire has a square or rectangular cross-section, to allow minimal space between windings, thereby to allow a greater number of coil turns and, thus, improved electrical efficiency.

Figure 9:
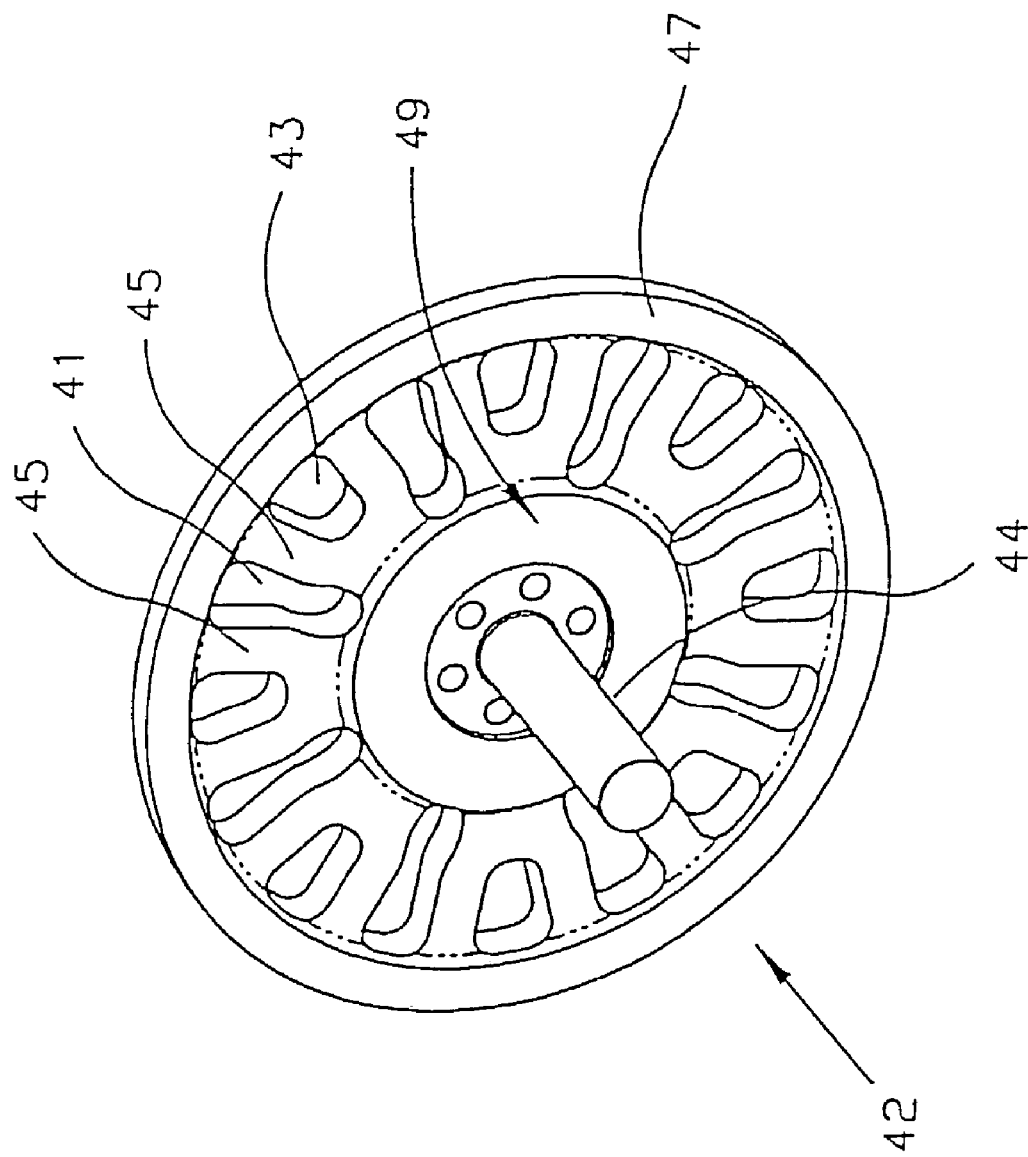
FIG. 9 is a perspective view of an embodiment of an actuator comprising an armature and a piston for the drive mechanism in FIGS. 3 and 4.

The drive mechanism 20 also includes an actuator member 40, which has an armature portion 42 and a piston portion 44. The actuator member is preferably made of a generally rigid, biocompatible and infusion medium compatible material, having a relatively high magnetic permeability such as, but not limited to, ferrous materials, ferritic stainless steel with high corrosion resistance, or the like. In the embodiment of FIGS. 3, 4 and 9, the actuator (with an armature portion 42 and a piston portion 44) is,formed as a single, unitary structure. In other embodiments as described below, the piston portion may be a separate structure with respect to the armature portion.

A perspective view of an example actuator member 40 is shown in FIG. 9, wherein the armature portion 42 of the actuator member has a round, disc shape, provided with at least one opening and, preferably, a plurality of openings as shown in the drawing. The openings in the illustrated example include a plurality of larger openings 41 which are elongated in the radial dimension of the armature, and a plurality of smaller openings 43, each disposed between a pair of larger openings 41. The sections 45 of the armature 42 between the openings 41 and 43 define radial struts coupling an annular outer section (or outer pole) 47 to an inner section (or inner pole) 49 of the armature.

As described in more detail below, the armature 42 cooperates with the inner and outer walls of the coil cup 32, to provide a flux path for electromagnetic flux. The spacing between the pole surfaces on the armature 42 and the pole surfaces on the coil cup walls define gaps in the flux path.

The radial struts 45 in the armature provide radial paths for electromagnetic flux between the outer and inner pole sections 47 and 49 of the armature. The openings 41 and 43 provide a passage for infusion medium to pass, as the actuator 40 is moved between retracted and forward stroke positions, to reduce resistance to the actuator motion that the infusion medium may otherwise produce. The configuration of openings is preferably designed to provide a sufficient conductor for electromagnetic flux and, yet minimize or reduce viscous resistance to actuator motion. To further reduce viscous resistance during actuator motion in the forward stroke direction, the inner and outer pole sections 47 and 49 may have textured surfaces facing the coil cup 38, to provide flow areas for medium between the pole sections 47, 49 and the coil cup 38 (or barrier 48 described below). In other embodiments, the actuator member 40 may be provided without openings separated by radial struts and, instead, may have a configuration as described in co-pending U.S. patent application Ser. No. 10/033,722 titled Infusion Device And Driving Mechanism And Process For Same With Actuator For Multiple Infusion Uses.

With reference to FIGS. 3 and 4, the actuator member 40 is arranged with the piston portion 44 extending through the axial channel 35 of the housing 30 and with the armature portion 42 positioned adjacent the open side of the coil cup 32. An actuator spring 46 is positioned to force the armature portion 42 of the actuator 40 in the direction away from the open side of the coil cup 32, to provide a gap between the armature 42 and the open side of the coil cup 32. A biocompatible and infusion medium compatible barrier 48 is located over the open side of the coil cup 32, between the armature 42 and the coil cup 32, to maintain a gap between those two members and/or to help seal the annular interior of the coil cup and coil 38. In other embodiments in which infusion medium may contact the coil, the barrier 48 may be omitted.

The actuator spring 46 in the illustrated embodiment comprises a coil spring disposed around the piston portion 44 of the actuator 40, adjacent the armature portion 42. One end of the coil spring abuts the armature portion 42 of the actuator, while the opposite end of the coil spring abuts a shoulder 39 in the piston channel 35 of the housing 30. In this manner, the actuator spring 46 imparts a spring force between the housing and the actuator 40, to urge the actuator toward its retracted position shown in FIG. 3.

In the illustrated embodiment, by using a coil spring 46 located around and coaxial with the piston portion 44 and disposed partially within the piston channel 35, the actuator spring may have minimal or no contribution to the overall thickness dimension of the drive mechanism. However, in other embodiments, actuator springs may have other suitable forms and may be located in other positions suitable for urging the actuator toward its retracted position shown in FIG. 3. The actuator spring 46 is preferably made of a biocompatible and infusion medium compatible material that exhibits a suitable spring force such as, but not limited to, titanium, stainless steel, MP35N cobalt steel or the like.

The drive mechanism 20 further includes a cover member 50 which attaches to the housing member 30, over the open side of the housing member and the barrier 48. The cover member 50 is preferably made of a generally rigid, biocompatible and infusion medium compatible material, having a relatively low magnetic permeability (being relatively magnetically opaque) such as, but not limited to, titanium, stainless steel, biocompatible plastic, ceramic, glass or the like.

The cover member 50 defines an interior volume 51 between the barrier 48 and the inner surface of the cover member. The armature portion 42 of the actuator member 40 resides within the interior volume 51 when the cover is attached to the housing, as shown in FIGS. 3 and 4. As described below, the armature 42 is moveable in the axial direction A within the volume 51, between a retracted position shown in FIG. 3 and a forward stroke position shown in FIG. 4. This movement is created by the action of electromagnetic force generated when a current is passed through the coil 38 and the mechanical return action of the actuator spring 46.

An adjusting plunger 52 is located within the cover 50, for contacting the armature 42 when the armature is in the fully retracted position shown in FIG. 3, to set the retracted position of the armature. In preferred embodiments, a seal may be disposed between the plunger 52 and the cover member 50, for example, but not limited to, a silicon rubber sealing ring. In further embodiments, a flexible diaphragm 59 (such as, but not limited to, a thin titanium sheet or foil) may be coupled to the inside surface of the cover 50 and sealed around the opening through which the plunger 52 extends. The diaphragm will flex to allow the plunger to define an adjustable retracted position and, yet, provide sealing functions for inhibiting leakage at the interface between the plunger 52 and the cover 50. In further preferred embodiments, once a proper armature position is set, the plunger is fixed in place with respect to the cover member, for example, by adhering the plunger to the cover member with one or more welds, adhesives or other securing methods.

The cover member 50 includes the inlet 27 of the drive mechanism, which has an inlet opening 54 in fluid flow communication with the interior volume 51, as described below. The inlet opening 54 connects in fluid flow communication with the reservoir of the infusion device 10 (FIG. 1), to receive infusion medium from the reservoir. Connection of the inlet opening 54 and the reservoir may be through suitable conduit (not shown), such as tubing made of suitable infusion medium compatible material, including, but not limited to titanium, stainless steel, biocompatible plastic, ceramic, glass or the like.

The inlet opening 54 provides a flow path to an inlet chamber 56 formed in the cover member 50, adjacent the inlet opening. A filter or screen member, such as a porous or screen material 58, may be disposed within the inlet chamber 56. The filter or screen member 58 is provided in a flow path between the inlet opening 54 and an inlet port 60 to the volume 51. A one-way inlet valve (not shown), to allow medium to flow into but not out of the interior volume 51 through the inlet, may also be provided in the flow path between the inlet opening 54 and the inlet port 60, or within the inlet port 60.

As shown in FIGS. 3 and 4, the piston portion 44 of the actuator 40 extends through the axial channel 35 in the housing 30, toward an outlet chamber 64 at the end of the axial channel 35. The channel 35 has an inside diameter which is larger than the outside diameter of the piston portion 44. As a result, an annular volume is defined between the piston portion 44 and the wall of the axial channel 35, along the length of the axial channel 35. Infusion medium may flow through the annular volume, from the volume 51 within the cover 50 to a piston chamber 65 located between the free end of the piston portion 44 and a valve member 66 of a valve assembly 67. In preferred embodiments, the radial spacing between the piston portion 44 and the wall of the channel 35 is selected to be large enough to provide a suitable flow toward the piston chamber 65 to refill the piston chamber 65 (during a return stroke of the piston portion).

The valve assembly 67 in the embodiment of FIGS. 3 and 4 includes the valve member 66, a valve spring 68 and support ring 70. The valve member 66 is located within the outlet chamber 64 and, as shown in FIG. 3, is positioned to close the opening between the axial channel 35 and the outlet chamber 64, when the actuator 40 is in the retracted position. In FIG. 4, the valve member 66 is positioned to open a flow passage between the axial channel 35 and the outlet chamber 64. The valve spring 68 is located within the outlet chamber 64, to support the valve member 66. The spring 68 imparts a spring force on the valve member 66, in the direction toward piston 44, urging the valve member 66 toward a closed position, to block the opening between the axial channel 35 and the outlet chamber 64.

The valve member 66 is preferably made of a generally rigid, biocompatible and infusion medium compatible material, such as, but not limited to, titanium, stainless steel, biocompatible plastic, ceramic, glass, gold, platinum or the like. A layer of silicon rubber or other suitable material may be attached to the rigid valve member material, on the surface facing the channel 35, to help seal the opening to the channel 35 when the valve member is in the closed position shown in FIG. 3.

The valve spring 68 is preferably made of a biocompatible and infusion medium compatible material that exhibits a suitable spring force such as, but not limited to, titanium, stainless steel, MP35N cobalt steel or the like. In the illustrated embodiment, the valve spring 68 has a generally flat, radial or spiral configuration. In preferred embodiments, the spring 68 includes radial arms that contact the interior of the outlet chamber in multiple locations around the periphery of the spring, to inhibit lateral or radial motion and improve stability of the spring. In further embodiments, a conical or belleville spring may be used. In yet further embodiments, other suitable valve spring configurations may be employed, including, but not limited to helical, conical, barrel, hourglass, constant or variable pitch springs or the like.

In the embodiment of FIGS. 3 and 4, the valve spring 68 is spaced from a valve cover 72 by the ring 70. The valve cover 72 is sealed to the housing 30, to enclose the outlet chamber 64. The ring 70 is disposed within the outlet chamber 64, between the spring 68 and the valve cover 72. With the valve member 66 supported between the spring 68 and the opening to the channel 35, the force imparted by the spring on the valve member is dependent, in part, on the characteristics and parameters of the spring and, in part, on the position of the spring within the outlet chamber. The ring 70 and the valve cover 72 are each preferably made of a generally rigid, biocompatible and infusion medium compatible material, such as, but not limited to, titanium, stainless steel, biocompatible plastic, ceramic, glass, gold, platinum or the like.

The thickness dimension $T_R$ of the ring 70 may be matched to fit within a recess within the outlet chamber, as shown in FIGS. 3 and 4. Alternatively, the thickness dimension $T_R$ of the ring 70 may be selected to define the position of the spring 68 within the outlet chamber, by defining the distance of the spring 68 relative to the valve cover 72 and relative to the opening between the axial channel 35 and the outlet chamber 64. A larger ring thickness $T_R$ will space the spring further from the valve cover 72 and closer to the opening to the axial channel 35, while a smaller ring thickness $T_R$ will space the spring closer to the valve cover 72 and further from the opening to the axial channel 35. In this manner, for a given spring 68, the force imparted by the spring on the valve member 66 to close the opening to the axial channel 35 (as shown in FIG. 3) may be selected or adjusted by selecting or adjusting the ring thickness $T_R$. The ring thickness $T_R$ and the spring characteristics are preferably selected to provide sufficient force to urge the valve member 66 into a suitably sealed or closed position as shown in FIG. 3, yet allow the movement force of the piston portion 44 (caused by electromagnetic force generated by the coil) to overcome the spring force and open the valve member 66 as shown in FIG. 4.

In the illustrated embodiment, the outlet chamber 64 comprises a cavity in the bottom of the housing 30, as shown in FIGS. 3, 4 and 7. Thus, in the illustrated embodiment, the outlet chamber cavity is generally centered within the same housing 30 that has the cavity holding the coil cup 32 and coil 38. With such an arrangement, the configuration of the drive mechanism 20 may be made with a relatively small thickness dimension (height dimension in the orientation shown in FIGS. 3 and 4) without compromising structural strength, as compared to alternative configurations in which the outlet chamber is formed with a separate member coupled to the housing 30.

As shown in FIG. 7, the outlet chamber cavity 64 may be provided in flow communication with an outlet 28 through a flow passage 74 and one or more accumulator cavities 78. The flow passage 74 comprises a channel which leads to the outlet 28 of the drive mechanism 20 and, eventually, to the device outlet 16 (FIG. 1). The outlet chamber cavity 64, flow passage 76, accumulator cavities 78 and flow passage 74 provide a flow path for infusion medium to flow from the outlet chamber to the device outlet 16, under pressure induced by operation of the drive mechanism 20. As shown in FIG. 7, the accumulator cavities 78, flow passage 76 and flow passage 74 may be provided lateral to the outlet chamber cavity 64 in the housing 30 to, thus, have minimal or no additional contribution to the overall thickness dimension T of the drive mechanism than that already required by the outlet chamber cavity 64.

Each accumulator cavity 78 forms a chamber which may contain one or more flexible, sealed packets, or accumulators, containing a compressible medium. In one preferred embodiment, each accumulator preferably comprises a packet made of a biocompatible and infusion medium compatible material of sufficient strength and flexibility to compress and expand under varying fluid pressures, such as, but not limited to stainless steel, titanium, platinum, which contains a compressible medium, such as, but not limited to a noble gas, such as argon or neon, or other suitable materials and media that provide a return pressure over a broad range of compression pressures. The accumulators may be used to help stabilize the flow rate of the drive mechanism and provide a relatively constant output pressure during drive operations, by acting as damping structures within the flow path between the outlet chamber 64 and the outlet 28.

Figure 10:
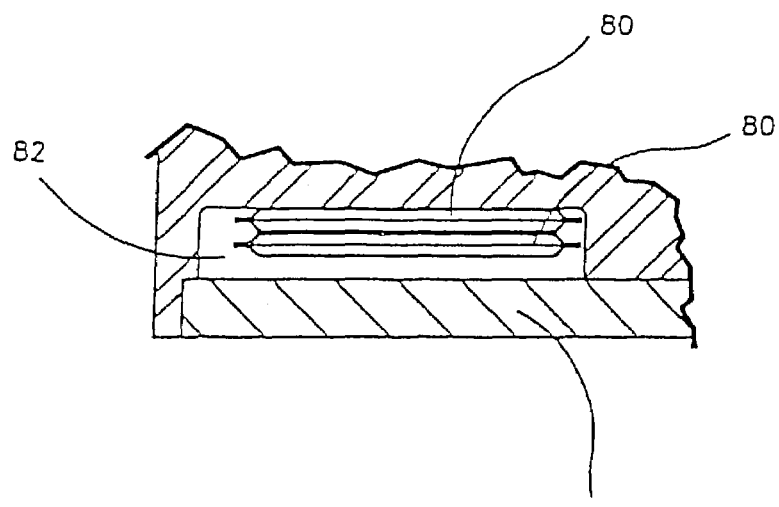
FIG. 10 is a partial cross-section view of a portion of a drive mechanism housing with an accumulator chamber.

For example, as shown in FIG. 10, one or more disc-shaped accumulators 80 may be stacked within each accumulator cavity, with or without an additional volume 82 for infusion medium. As the pressure of the infusion medium within the accumulator cavity increases, the accumulators 80 compress to increase the volume 82. Similarly, as the infusion medium pressure decreases, the accumulators 80 may expand and decrease the volume 82. In this manner, the accumulators 80 inhibit sharp changes in infusion medium pressure and provide a dampening mechanism for dampening pressure changes to allow a relatively constant pressure flow through the outlet 28, during operation of the drive mechanism 20. While the illustrated embodiment employs two accumulator cavities, each having two accumulators, other embodiments may employ any suitable number of accumulator cavities and accumulators. Other embodiments may employ cavities 78, without accumulators or with other mechanisms that provide volume adjustment or flow smoothing capabilities, including, but not limited to, bellows structures, sponge-type structures, fluid accumulators or the like. Yet other embodiments, in which the maintenance of a relatively constant outlet pressure is not a concern, may omit accumulator cavities and accumulators, such that the outlet chamber is directly coupled to the outlet port.

Figure 5:
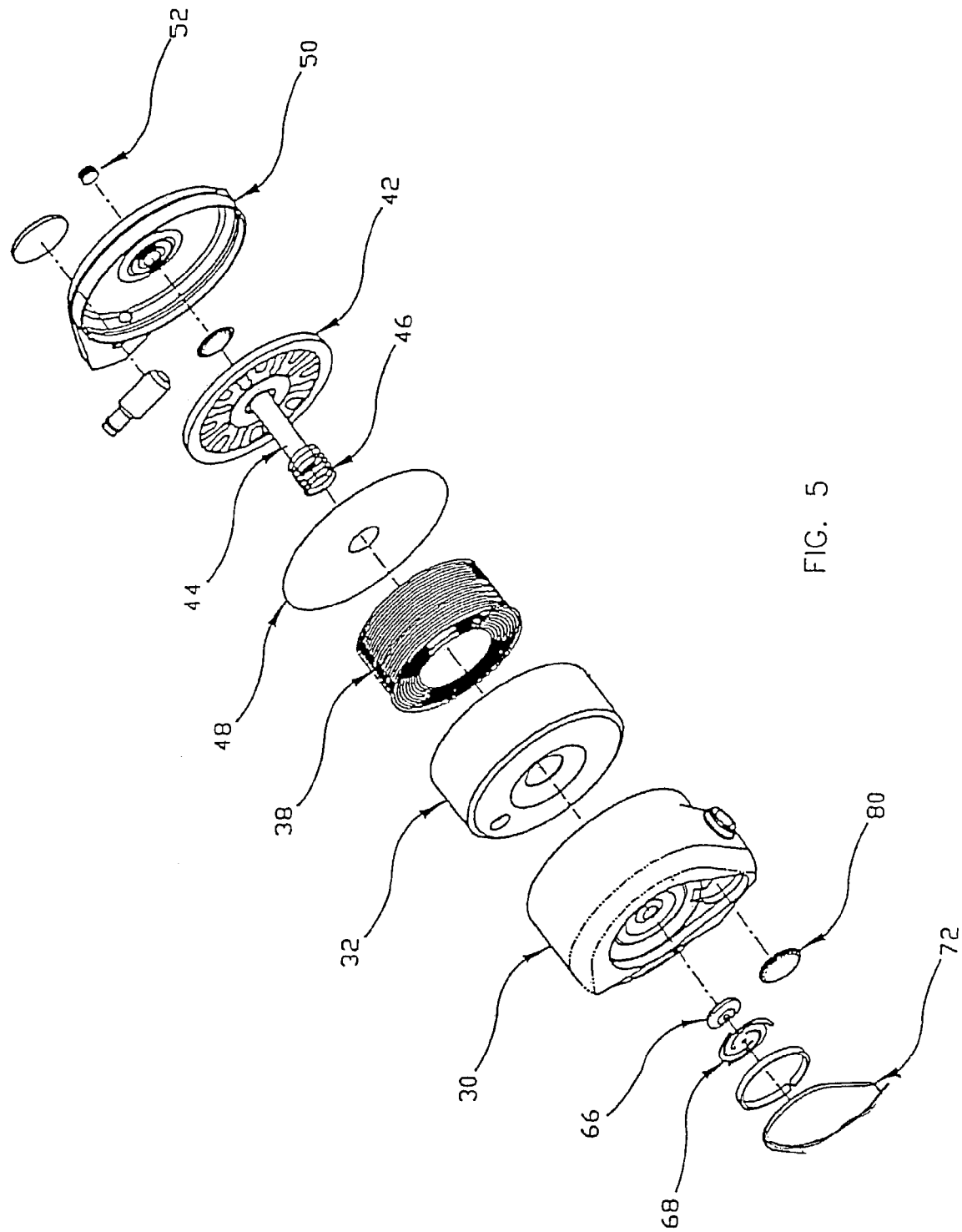
FIG. 5 is a an exploded view of an embodiment of the drive mechanism shown in FIGS. 3 and 4.

A drive mechanism as shown in FIGS. 3 and 4 may be constructed by providing components as shown in FIG. 5 and assembling the components in any suitable sequence. The components may be made according to any suitable process including, but not limited to molding, machining, extruding, sintering, casting, combinations thereof or the like.

The coil 38 may be inserted into the annular interior 33 of the coil cup 32, with the coil leads extended through a coil lead opening 84 in the coil cup. The coil may be impregnated or partially impregnated with a fill material of epoxy or the like, for adhering the coil to the coil cup and for sealing or partially sealing the coil. The fill material may also be used to adhere the barrier plate to the coil members, to avoid warping or bulging of the barrier plate after assembly.

The coil cup 32 and coil 38 may be inserted into the interior 31 of the housing 30, with the coil leads (which may be wire leads or flexible conductive tabs) extending through a coil lead opening 86 in the housing 30. In preferred embodiments, the coil cup and housing are configured to provide a tight, friction fit therebetween, without requiring additional means of adhering the two components together. In other embodiments, the coil cup 32 and housing 30 may be coupled together by any suitable adhesive material or other adhering methods, including, but not limited to welding, brazing, of the like.

The barrier 48 may be placed over the coil, coil cup and housing sub-assembly. The barrier 48 may be adhered to the housing by one or more adhering points or continuously along the circumference of the barrier 48, with any suitable adhesive material or other adhering methods, including, but not limited to welding, brazing, soldering or the like. Alternatively, or in addition, the barrier 48 may be held in place by a shoulder portion of the cover 50, as shown in FIGS. 3 and 4. In addition, as noted above, the barrier 48 may be adhered to the coil 38 by fill material in the coil. In preferred embodiments, the barrier 48 is held in a generally flat relation relative to the coil cup and coil. To enhance this flat relation, the coil cup and housing may assembled together and then machined to planarize the barrier contact surfaces, prior to inserting the coil in the coil cup and prior to adding fill material to the coil.

Once the barrier 48 is placed over the coil, coil cup and housing, the actuator 40 may be added to the sub-assembly. First, however, the actuator spring 46 is placed around the piston portion 44, adjacent the armature portion 42 of the actuator. Then the free end of the piston portion 44 is passed through the axial channel 35 of the housing 30, with the armature end of the actuator arranged adjacent the barrier 48.

The cover member 50 may then be disposed over the armature end of the actuator and secured to the housing 30. In preferred embodiments, the cover member 50 is adhered to the housing by one or more adhering points or continuously along the circumference of the cover member 50, with one or more welds or any other suitable adhering methods, including, but not limited to adhesive materials, brazing or the like. The inlet filter 58 and inlet cover 62 may be pre-assembled with the cover member 50, prior to adding the cover member to the sub-assembly. Alternatively, the filter 58 and inlet cover 62 may be added to the cover member 50 after the cover member 50 is assembled onto the housing 30. In preferred embodiments, the filter 58 is disposed within the inlet chamber 56 and, then, the inlet cover 62 is adhered to the cover member 50 by one or more adhering points or continuously along the circumference of the inlet cover, with one or more welds or any other suitable adhering methods, including, but not limited to adhesive materials, brazing or the like.

The valve side of the drive mechanism may be assembled before or after the above-described components are assembled. On the valve side of the drive mechanism, the valve member 66 is disposed within the outlet chamber cavity 64 of the housing 30, adjacent the opening to the axial channel 35. The valve spring 68 is then disposed within the outlet chamber cavity 64, adjacent the valve member 66. The ring 70 is then disposed in the cavity 64, adjacent the spring 68. Any suitable number of accumulators may be placed within each of the accumulator cavities 78. The valve cover 72 may then be placed over the outlet chamber cavity 64 and accumulator cavities 78. In preferred embodiments, the housing 30 is provided with a recess 88 around the periphery of the cavities that form the outlet chamber cavity 64, accumulator cavities 78, outlet port 74 and flow passage 76, for providing a seat for the valve cover 72. In this manner, the valve cover 72 fits within the recess 88, flush with the housing 30. Also in preferred embodiments, the valve cover 72 is adhered to the housing 30 by one or more adhering points or continuously along the circumference of the valve cover, with one or more welds or any other suitable adhering methods, including, but not limited to adhesive materials, brazing or the like.

The volume of the piston chamber 65, the compression of the actuator spring 46 and the position of the actuator 40 in the retracted position shown in FIG. 3 may be adjusted by the adjusting the position of the adjusting plunger 52. In one preferred embodiment, the adjusting plunger includes a threaded cylindrical member, which engages corresponding threads in a plunger aperture in the cover member 50, to allow adjustment in a screw-threading manner. The diaphragm 59 under the plunger 52 contacts the armature portion 42 of the actuator, inside of the cover member 50. The other end of the plunger 52 may be provided with a tool-engagement depression, for allowing engagement by a tool, such as a screw-driver, Allen wrench or the like, from outside of the cover member 50. By engaging and rotating the plunger 52 with a suitable tool, the depth that the plunger extends into the cover member 50 may be adjusted, to adjust the retracted position of the armature portion 42 relative to the barrier 48 (to adjust the gaps between the pole sections 47, 49 of the armature and pole sections formed by the coil cup 32, when the actuator is in the retracted position of FIG. 3). In one preferred embodiment, adjustments of the plunger 52 are made during manufacture. In that embodiment, the adjusted position is determined and set by welding or otherwise adhering the plunger 52 in the adjusted position during manufacture. In other embodiments, the plunger 52 is not set and welded during manufacture, to allow adjustment of plunger 52 after manufacture.

The resulting drive mechanism 20 may, therefore, be constructed to provide a relatively thin form factor and, yet provide a reliable operation that can meter relatively precise volumes of infusion medium at relatively constant flow pressure. A number of features can provide, or be combined to contribute to, reductions in the thickness form factor of the drive mechanism. For example, the coaxial arrangement of components such as the piston portion 44 and the coil 38, with a flow channel formed within the piston channel 35, can be implemented with a smaller thickness form factor (in the vertical dimension of FIGS. 3 and 4) than alternative arrangements in which those components are arranged adjacent each other in the thickness dimension.

Furthermore, the arrangement of an inlet volume 51 on one side of the coil 38 and an outlet chamber 64 on the opposite side of the coil 38, with a flow passage through the channel 35 in the coil 38 can also contribute to a reduction in the required thickness dimension of the drive mechanism, by allowing the coil 38 and channel 35 to share a common portion of the thickness dimension. The arrangement of the armature portion 42 to move within the inlet volume 51 allows those features to share a common portion of the thickness dimension. The arrangement of the outlet chamber 64 in a central location within the same housing that has the coil cup cavity allows those features to be formed in relatively close proximity to each other in the thickness dimension. The arrangement of the outlet chamber, outlet port and accumulator cavities in the housing 30 allows those features to share a common portion of the thickness dimension of the drive mechanism. Further features, including recessed shoulders 39 for the actuator spring 46, the use of a relatively flat valve spring 68 and general attention to minimizing thickness dimensions of components, where possible, can also contribute to reductions in the overall thickness dimension of the drive mechanism.

Operation of First Drive Mechanism Embodiment with Positive Pressure Reservoir As described above, embodiments of the present invention may employ a reservoir containing (or capable of containing) an infusion medium under positive pressure. The infusion medium is provided to the inlet 54 of the drive mechanism 20, by the positive pressure provided by the reservoir. Preferably, such positive pressure is provided by a propellant medium contained within the reservoir, as described above, without the requirement of electrical energy to create the positive pressure.

In this manner, infusion medium may be provided to the drive mechanism 20 under positive pressure via suitable conduit (not shown) to inlet opening 54. In operation, the drive mechanism 20 employs electromagnetic and mechanical forces to move between retracted (FIG. 3) and forward (FIG. 4) positions, to cause infusion medium to be metered out of the mechanism in a controlled manner. The infusion medium then enters inlet chamber 56 under the positive pressure and enters volume 51 via inlet port 60. The medium then flows under positive pressure through the annular volume, from the volume 51 within the cover 50 to piston chamber 65. In the retracted position, the spring 46 urges the actuator 40 toward its retracted position shown in FIG. 3 preventing infusion medium in piston chamber 65 from entering outlet chamber 64. The spring force of spring 46 is chosen such that it is sufficient to oppose the force exerted on it by the medium under the positive pressure of the positive pressure reservoir. When the coil 38 is energized to overcome the spring force of spring 46, the actuator 40 moves to its forward stroke position and opens the valve member 66 as shown in FIG. 4. The movement of the actuator to the forward position allows medium to discharge through outlet chamber 64 and out the outlet 28.

More specifically, when the coil 38 is de-activated (not energized or not energized in a manner to overcome the spring force of spring 46), the actuator 40 is held in its retracted position (FIG. 3) under the force of the spring 46. When the coil is de-activated immediately following a forward stroke, the spring 46 moves the actuator 40 to the retracted position of FIG. 3, from the forward position shown in FIG. 4. In some embodiments the actuator 40 may have openings 41 and 43 in the armature portion 42 to provide passages for medium to pass and, thus, reduce viscous drag on the actuator. As a result, the actuator 40 may move to its retracted position (FIG. 3) relatively quickly.

In the retracted position, a gap is formed between each of the annular pole surfaces 91 and 93 defined by the inner and outer walls 90 and 92 of the coil cup 32 and a respective annular surfaces of the inner and outer pole sections 49 and 47 of the actuator's armature portion 42. In particular, with reference to FIG. 3, a first gap 94 is formed between the annular pole surface 91 of the inner cup member wall 90 and the annular surface of the inner pole section 49. A second gap 95 is formed between the annular surface 93 of the outer cup member wall 92 and the annular surface of the outer pole section 47.

When the coil 38 is energized (or energized in a manner to overcome the spring force of spring 46), the actuator 40 is forced in the direction to close the gaps 94 and 95 and moves to its forward position (FIG. 4) under the influence of electromagnetic flux generated by the energized coil. In particular, the coil may be energized by passing an electrical current through the coil conductor to create electromagnetic flux. The electromagnetic flux defines a flux path through the coil cup walls, across the gaps 94 and 95 and through the armature portion of the actuator. The electromagnetic flux provides an attraction force between the annular surfaces 91, 93 of the coil cup 32 and the annular surfaces of the armature's pole sections 47, 49, to overcome the spring force of spring 46 and draw the armature 42 toward the coil cup.

As the armature portion 42 of the actuator is drawn toward the coil cup 32, the piston portion 44 of the actuator is moved axially through the channel 35, in the direction toward the outlet chamber 64. With the coil energized, the piston portion 44 continues to move under the action of the armature, until a mechanical stop is reached, for example, mechanical contact of the actuator 40 with the barrier 48, a portion of the housing 30 or cover member 50. In other embodiments, the motion may continue until the return force of the spring and fluid pressure overcomes the electromagnetic force provided by energizing the coil.

The movement of the piston portion 44 towards the stopping point reduces the volume of the piston chamber 65 and increases the pressure within the piston chamber until the pressure is sufficient to overcome the force of the valve spring 68. As the valve spring force is overcome by the pressure within the piston chamber, the valve member 66 is moved toward an open position, away from the opening between the piston chamber 65 and outlet chamber 64. When the valve member 66 is in the open position, medium is discharged through the outlet chamber 64 and outlet 28 (FIG. 7).

When the coil is deactivated and the piston portion 44 is moved back to its retracted position, the pressure in the piston chamber 65 reduces and the valve member 66 is reseated under the action of the valve spring 68, preventing further infusion medium from discharging through outlet 28.

In this manner, energization of the coil 38 to move the actuator 40 to its forward position (FIG. 4) causes a measured volume of medium to be discharged from the outlet. Thus, valve member 66 functions as a measuring or "metering" valve. As described above, when the coil 38 is de-energized, the actuator 40 is returned to the retracted position (FIG. 3) under the force of spring 46. Accordingly, the coil 38 may be energized and de-energized by a controlled electronic pulse signal, where each pulse may actuate the drive mechanism 20 to discharge a measured volume of medium. In preferred embodiments, the coil 38 may be electrically coupled to an electronic control circuit (not shown) to receive an electronic pulse signal from the control circuit for example, in response to a sensor signal, timer signal or other control signal input to the control circuit.

According to embodiments of the present invention, an additional valve 69 may also be provided to open and close the fluid flow path between the outlet chamber 64 and the infusion site to provide additional protection against unwanted discharge of infusion medium from the infusion device. In preferred embodiments, the additional check valve 69 may be located within outlet chamber 64. However, in other embodiments, the check valve may be located anywhere in the flow path between the outlet chamber 64 and the infusion site, including within outlet 28, within a catheter 71 attached between outlet 28 and the infusion site or in any other suitable location. FIG. 7 illustrates possible positions for the additional check valve 69 according to some of the preferred embodiments: within the outlet chamber 64; within the outlet 28; and, within the catheter 71.

According to embodiments of the present invention, the check valve 69 may be any suitable valve known in the art that protects against undesired leakage from the infusion device. In one embodiment, the check valve 69 may include a valve member compressed against a valve opening. As a non-limiting example, a spring loaded ball valve known in the art may be used. Typically, a spring loaded ball valve includes a valve seat and a ball, which is tension-biased against the seat, such as by the employment of a spring of suitable tension. The valve seat may be comprised of any suitable material, including, but not limited to, metal, ceramic, plastic, silicone rubber and the like. Similarly, the ball may be comprised of any suitable material, including, but not limited to, metal, sapphire, ceramic, plastic and the like.

According to embodiments of the present invention, at pressures of or below the pressure provided by the positive pressure reservoir, the check valve remains in its off state and closes off any fluid leakage that may develop between the outlet chamber 64 and the infusion site. Pressures of or below the positive pressure provided by the positive pressure reservoir are not high enough to displace the ball from its fluid tight fit against the seat of the valve. However, when the coil 38 is energized as described above, the pressure within the piston chamber is sufficient to overcome the force of the valve spring 68 and medium is discharged through the outlet chamber 64. As the medium is discharged through the outlet chamber 64, the medium flows towards the check valve under a pressure sufficient to overcome the check valve spring force and open the check valve by moving the ball away from the valve seat, allowing fluid flow to the infusion site.

In the embodiment described above, the check valve is opened by a sufficient pressure exerted upon it. However, in other embodiments, other types of check valves may be used. For example, a controllable valve may be electrically coupled to an electronic control circuit to receive an electronic pulse signal from the control circuit for example, in response to a sensor signal, timer signal or other control signal input to the control circuit. The controllable valve may be opened or closed by means of this electronic pulse signal.

In one embodiment, a magnetically activated spring-loaded ball valve may be used. In this embodiment, the ball could be removed from the valve seat by the use of the magnet to permit the flow of medium. The ball valve may have sufficient tension to be placed in the closed position, but insufficient to prevent the ball valve from moving to the open position when magnetically activated, for example by means of an energized coil.

In some embodiments, the electronic pulse signal may be provided to the check valve simultaneously with the electronic pulse signal that is provided to energize the coil 38, as described above. In this manner, both the valve member 66 and the check valve may open simultaneously to allow the medium to flow from the outlet chamber 64 to the infusion site.

In other embodiments, in addition to the check valve, or in the alternative, a conventional pressure regulating valve may be included in the medium flow path. The pressure at which medium flows through the flow path may be advantageously sensed by the pressure regulating valve placed at a suitable location in the flow path. In one embodiment, the pressure regulating valve may have a low pressure cut-off point approximately equal to the pressure exerted by the positive pressure reservoir on the medium. Any medium flowing at a pressure below this low pressure cut-off point will not pass through the pressure regulating valve. In this manner, any undesired leakage of the medium may be minimized.

However, in other embodiments, an additional check valve or pressure regulating valve may be omitted and, instead, the drive mechanism 20 may be configured as a single valve mechanism, employing a single outlet valve (for example, outlet valve assembly 67 described above) and no additional check valve or pressure regulating valve. However, according to these other embodiments, other measures may be taken in order to minimize the possibility of undesired leakage of the infusion medium. For example, the tension of the valve spring 68 may be increased in order to provide a tighter seal on the opening between the piston chamber 65 and outlet chamber 64.

According to further embodiments of the present invention, a bacterial particulate filter may be included in the flow path of the infusion medium for trapping particulate matter in the infusion medium. Any suitable bacterial particulate filter known in the art may be used with embodiments of the present invention.

When the actuator is stopped, for example, by contact with the barrier 48 or other mechanical stop structure, the coil current/voltage relationship changes. In preferred embodiments, control electronics (not shown) are connected to detect the change in coil current or voltage and deactivate the coil when the armature reaches the stop point. In this manner, the coil may be energized for only as long as the electromagnetic flux generated by the coil is providing useful work. Once the actuator motion is stopped and no further useful work is provided by the electromagnetic flux, the coil may be deactivated to reduce or minimize power consumption requirements of the drive mechanism.

Second Drive Mechanism Embodiment and Operation

Figure 11:
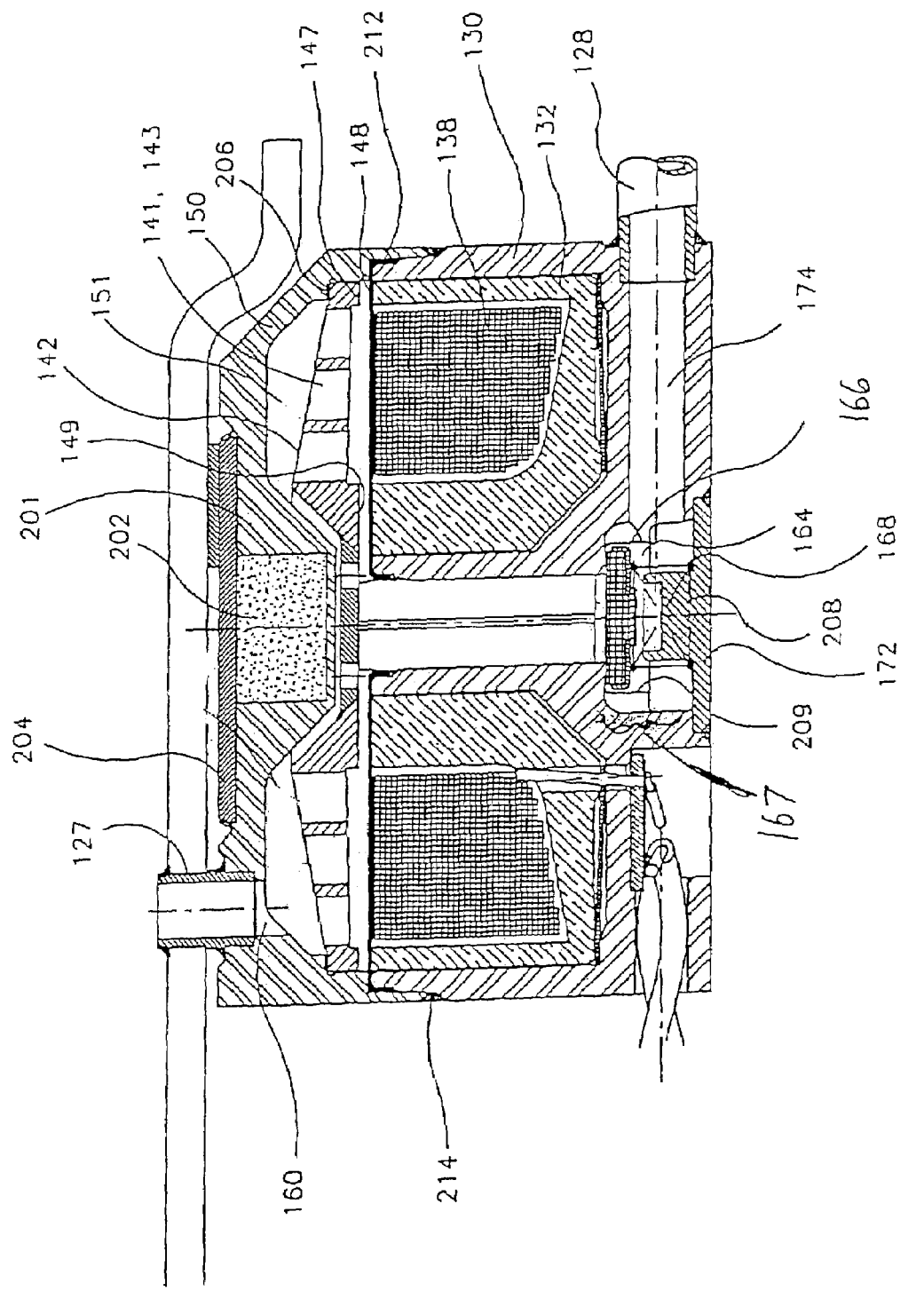
FIG. 11 is a cross-section view of another example embodiment of the drive mechanism of FIG. 2, in a retracted position or state.
Figure 12:
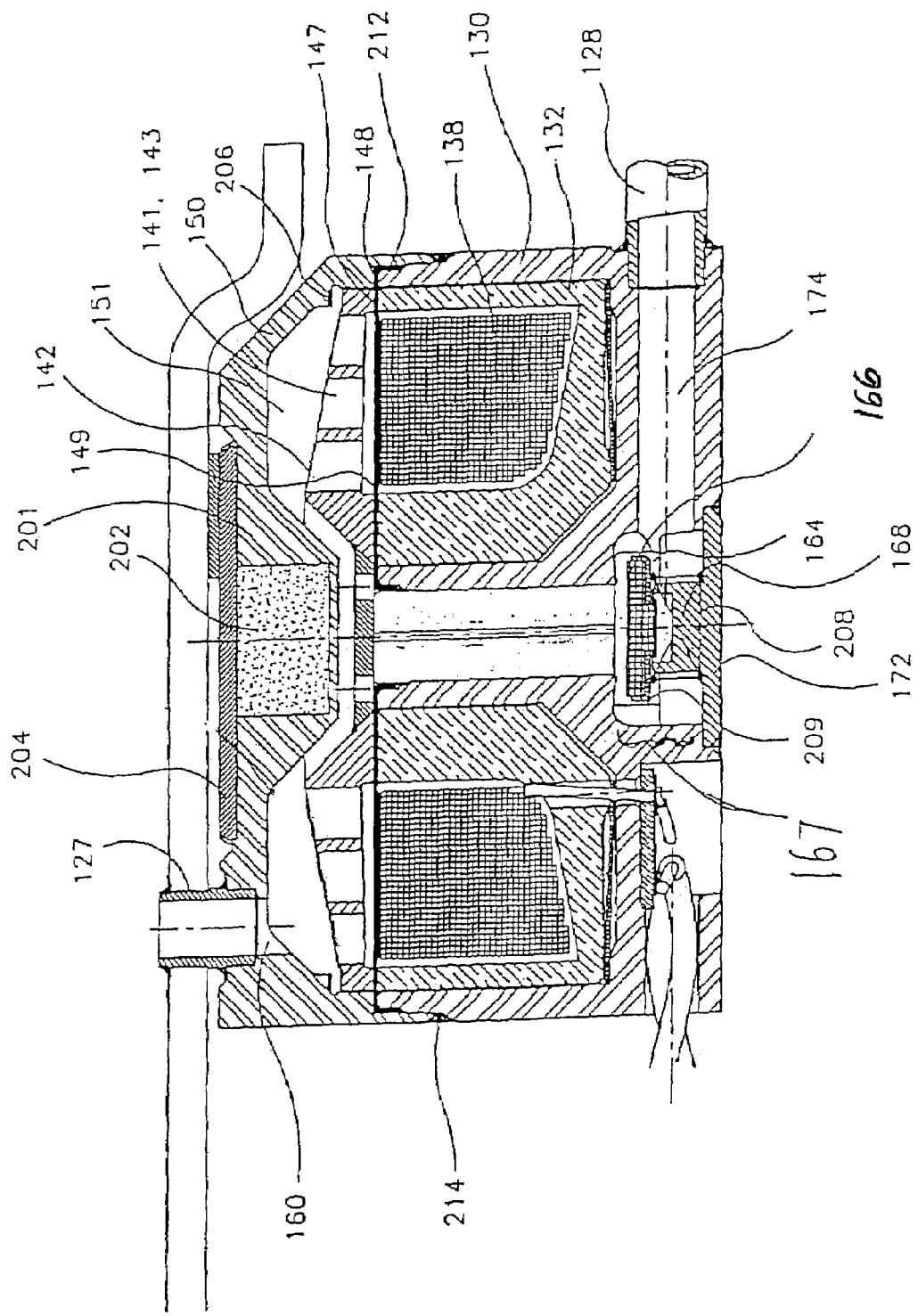
FIG. 12 is a cross-section view of the example drive mechanism embodiment of FIG. 11, in a forward stroke position or state.

A drive mechanism 120 according to a further embodiment of the invention is shown, in cross-section, in FIGS. 11 and 12. Similar to the drive mechanism 20 described above, the drive mechanism 120 may be coupled to a positive pressure reservoir, for receiving infusion media under positive pressure.

FIG. 11 shows the drive mechanism 120 in a retracted position, while FIG. 12 shows the drive mechanism 120 in a forward position. Many aspects and features of the mechanism 120 are similar to corresponding aspects and features of drive mechanism 20 and for which reference is made to the above description of drive mechanism 20. Other aspects and features of drive mechanism 120 that differ from drive mechanism 20 are apparent from the drawings and the description below.

The drive mechanism 120 may be employed in the device 10 of FIG. 1, in a manner similar to that described above with respect to drive mechanism 20. Similar to the drive mechanism 20 of FIGS. 3 and 4, the drive mechanism 120 of FIGS. 11 and 12 includes an inlet 127, an outlet 128, a housing 130, a coil cup 132, an axial channel 135, a coil 138, an armature 142, a piston 144, a barrier member 148, a cover member 150 having an interior volume 151, a valve member 166, an inlet port 160, an outlet chamber 164, a piston chamber 165, a valve spring 168, a valve cover 172, and an outlet port 174. These features provide functions that correspond to the functions of the corresponding features of drive mechanism 20 of FIGS. 3 and 4 (shown in FIGS. 3 and 4 with corresponding reference numbers, without the hundredth digit). Insofar as these features have structural and operational similarities reference is made to the above descriptions of corresponding features, to avoid duplication of descriptions.

However, as noted above, various differences between the embodiments 20 and 120 are apparent from the drawings. One difference relates to the armature 142 and piston 144 which, together, form an actuator. In the embodiment of FIGS. 11 and 12, the armature and piston portions of the actuator are separate elements, while in the embodiment of FIGS. 3 and 4 described above, the piston and armature are portions of a single, unitary actuator structure.

In addition, the piston 144 has a central flow passage 145 extending between the two piston ends and open on each end to allow infusion medium to flow through the piston and, thus, through the channel 135. In the illustrated embodiment, a single flow passage 145 is provided along the central axis of the piston 144. In other embodiments one or more flow passages may be provided in a non-axial arrangement with or without an axial flow passage. With one or more central flow passages 145 through the piston 144 to allow passage of infusion medium through the channel 135, the spacing between the piston 144 and the wall of the channel 135 may be relatively small. As a result, the speed of refilling of the piston chamber may be increased.

The armature 142 has openings 141, 143 through which infusion medium may pass. While not shown in FIGS. 11 and 12, the openings 141, 143 may be arranged to provide radial flux conduction paths on the armature, as described above with respect to openings 41 and 43 in the armature 42 of FIGS. 3 and 4. In addition, the armature 142 may include further openings adjacent the central piston contact location.

The armature 142 has a tapered surface to define a generally frusto-conical shape having a thin cross-section at its outer periphery or outer pole 147, relative to the cross-section at the inner pole 149. The tapered surface of the armature 142 has a central indentation, in which an extended central portion 201 of the cover member 150 extends. A permanent magnet 202 is disposed within the central portion of the cover member 150 and a magnet cover 204 is attached to the cover member 150, over the magnet 202.

The armature 142 and piston 144 are drawn toward the retracted position shown in FIG. 3, by the attraction force of the permanent magnet 202. As a result, a spring (such as spring 46 in the embodiment of FIGS. 3 and 4) is not needed. However, further embodiments may employ various combinations of one or more permanent magnets and springs for urging the armature 142 and piston 144 toward the retracted position. In the retracted position, the armature 142 abuts a shoulder 206 on the cover member 150. In further embodiments, instead of abutting shoulders 206, the armature 142 abuts the extended central portion 201 of the cover member 150.

Figure 13:
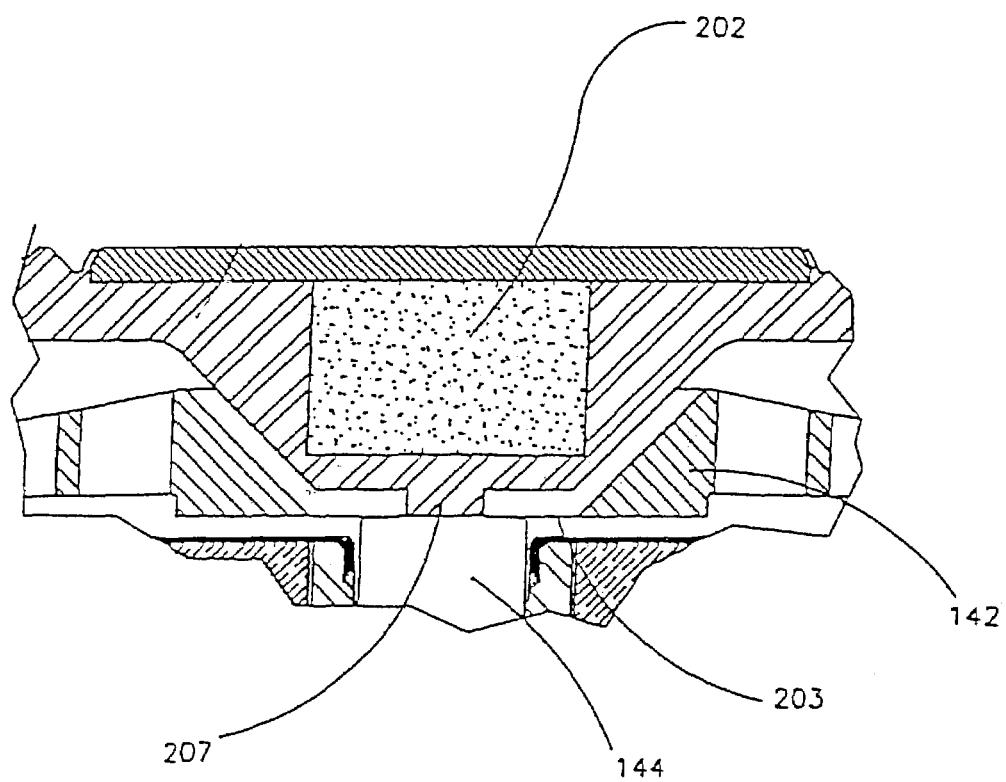
FIG. 13 is a partial cross-section view of a portion of the drive mechanism cover, armature and piston, according to a further embodiment of the invention.

In embodiments employing a magnet 202, the armature 142 may be configured with a central section 203 formed of a non-magnetic material, such as stainless steel, biocompatible plastic, ceramic, glass or the like, to allow the magnetic flux from the magnet 202 to have a greater attraction action on the piston 144. The portion of the armature 142 outward of the central section 203 is preferably made of a magnetically permeable material, as described above with respect to armature 42. In further embodiments, the central section 203 of the armature may be open. In such embodiments, the central extended portion 201 may include a further extension, shown at 207 in FIG. 13, to provide a stop for the piston 144 in its retracted position.

In yet further embodiments, an adjusting plunger, such as plunger 52 described above with respect to the embodiment of FIGS. 3 and 4, may be disposed through the cover member 150 to provide an adjustable stop for the armature 142 in the retracted position. For example, an adjustment plunger may extend through an aperture (not shown) formed in the magnet 202 or formed elsewhere in the cover member 150, to abut the armature in its retracted position.

In the embodiment of FIGS. 11 and 12, the inlet 127 and inlet port 160 extend vertically with respect to the orientation shown in those figures. However, other embodiments may employ a horizontal inlet port arrangement with respect to the orientation of the figures, such as shown in FIGS. 3 and 4. Likewise, embodiments as shown in FIGS. 3 and 4 may be implemented with a vertical inlet port arrangement as shown in FIGS. 11 and 12. Of course, other suitable inlet port arrangements may be employed without detracting from further aspects of the drive mechanism described herein.

The outlet chamber 164 in FIGS. 11 and 12 contains a valve assembly 167 comprising a valve member 166 and a valve spring 168. The spring 168 is a coil spring, rather than the flat, spiral spring 68 of FIGS. 3 and 4. The coil spring 168 is disposed around a central extended portion 208 of the valve cover 172 and, in the retracted position (FIG. 11), extends beyond the central extended portion 208 to support the valve member 166 in a spaced relation with respect to the central extended portion 208. In the forward position (FIG. 12), the valve member 166 compresses the coil spring and abuts against the central extended portion 208 of the valve cover 172. The interior walls of the outlet chamber 164 are provided with ribs or flutes 209 to help guide the valve member 166 between open and closed positions (shown in FIGS. 11 and 12, respectively).

While a coil spring arrangement is shown in FIGS. 11 and 12 and a flat spring arrangement is shown in FIGS. 3 and 4, either a coil or flat spring arrangement may be employed in either of those embodiments. A flat spring arrangement may provide a thinner form factor and adjustment capabilities by selecting or adjusting the thickness of the ring 70, as described above. However, a coil spring arrangement may provide a more stable support for embodiments in which the piston portion of the actuator is separable from the armature portion.

The barrier member 148 in FIGS. 11 and 12 may have folded inner and outer edges 210 and 212, which fold over the inner and outer walls of the housing 130. The inner and outer housing walls are formed with annular indentations for receiving the folded edges 210 and 212 of the barrier member 148. The folded edges of the barrier member enhance the sealing capabilities of the barrier member. In addition, the folded edges allow the barrier member to be welded, or otherwise adhered, to the housing 130 along a surface 214 on the lateral side of the housing's outer wall. The folded edges allow the barrier to be machined (for example, lapped) flat, after welding. While a folded edge barrier member arrangement is shown in FIGS. 11 and 12 and a flat barrier member arrangement is shown in FIGS. 3 and 4, either a folded edge or flat arrangement may be employed in either of those embodiments.

The drive mechanism 120 operates similar to the drive mechanism 20 described above. However, unlike the armature 42 and piston 44 in the drive mechanism 20, the armature 142 and the piston 144 of the drive mechanism 120 are capable of moving independently and infusion medium is allowed to flow through the passage 145 in the piston when the piston is physically separated from the armature.

Similar to the embodiment described above, the drive mechanism 120 employs electromagnetic and mechanical forces to move between retracted (FIG. 11) and forward (FIG. 12) positions, to cause infusion medium to be metered out of the mechanism in a controlled manner. In the retracted position, the magnet 202 urges both the armature 142 and the piston 144 toward their retracted positions shown in FIG. 11.

When the coil 138 is energized, the armature 142 is attracted to the coil cup 138 by electromagnetic flux as described above. The attraction force is sufficient to overcome the force of magnet 202 and cause the armature to move and close the gap in the electromagnetic flux path between the armature 142 and the coil cup 132. As the piston 144 is in contact with the armature 142, the piston also moves, reducing the volume of the piston chamber 165. As the piston 144 moves toward its forward position, the pressure in the piston chamber 165 increases until it is sufficient to overcome the force of the spring 168 and move the valve member 166 to the open position. When the valve member is opened, infusion medium within the piston chamber 165, passage 145 and within the volume between the piston 144 and the wall of the channel 135 is discharged into the outlet chamber and through the outlet port 174.

The piston 144 continues to move under the force of the armature 142 until the armature 142 contacts the barrier 148 or a mating face (not shown) of the housing 130 or cover 150.

When the coil 138 is de-energized, the ferro-magnetic armature 142 and piston 144 attracted by the magnet 202, to move from the forward stroke position of FIG. 11, toward the retracted position of FIG. 12.

As the piston 144 moves to the retracted position, the pressure within the piston chamber 165 reduces to help draw medium into the piston chamber and to allow the valve member 166 to close. After the piston 144 completes its return stroke, it is again in contact with the armature 142 and the passage 145 in the piston is again blocked by the armature 142. The piston is then ready for its next forward stroke.

Configurations described herein allow the infusion device to include a piston-type drive mechanism in combination with a positive pressure reservoir which avoids the effort and expense required in closely controlling tolerances relating to tube alignment and roller occluding force on the tubes that is required for peristaltic drive mechanisms. Configurations described herein also allow more efficient use of electrical power and increased functional longevity by avoiding the consumption of electrical power associated with mechanical friction produced by passing a roller or rollers over a tube surface in peristaltic or roller pumps.

The foregoing description of the preferred embodiment of the invention has been presented for the purposes of illustration and description. It is not intended to be exhaustive or to limit the invention to the precise form disclosed. Many modifications and variations are possible in light of the above teaching.

What is claimed is:

1. An infusion medium delivery device comprising:
  a reservoir for containing infusion medium under positive pressure;
  a drive device having:
    an inlet for receiving infusion medium under positive pressure;
    a piston channel for communication of infusion medium received by the inlet;
    a coil surrounding the piston channel;
    an armature disposed adjacent the coil, on one side of the piston channel;
    an outlet chamber disposed adjacent the coil, on the opposite side of the piston channel relative to the armature for receiving infusion medium from the channel;
    a piston located within the piston channel and moveable axially within the piston channel for allowing infusion medium to enter the outlet chamber under positive pressure; and
    an outlet in flow communication with the outlet chamber, for discharging a metered amount of infusion medium from the outlet chamber;
  a first valve member positioned downstream of the piston channel in a flow path of infusion medium, said first valve member moveable between opened and closed positions to selectively open and close one end of the piston channel to the outlet chamber, said one end of the piston channel closed to the outlet chamber when the first valve member is in the closed position; and
  a second valve member in fluid communication with the first valve member and positioned downstream of the first valve member in the flow path of infusion medium, the second valve member being moveable between opened and closed positions;
  wherein the first valve member is configured such that the first valve member is in the opened position at least when the metered amount of infusion medium beams to be discharged from the outlet chamber.

2. The device as recited in claim 1, wherein the second valve member comprises a pressure regulating valve in fluid communication with the first valve member and positioned downstream of the first valve member in a flow path of the infusion medium for regulating flow of the infusion medium.

3. The device as recited in claim 2, wherein the pressure regulating valve has a low pressure cut-off point approximately equal to the positive pressure exerted by the positive pressure reservoir on the infusion medium.

4. The device as recited in claim 1, wherein the first valve member is moveable between the opened and closed positions to selectively allow and inhibit fluid flow between the inlet and the outlet.

5. The device as recited in claim 1, wherein the first valve member is moveable in response to axial movement of the piston within the piston channel.

6. The device as recited in claim 1, further including a housing containing the coil and the outlet chamber, the housing having at least one fluid flow damping means or accumulator disposed in a flow path between the outlet chamber and the outlet, for reducing flow pressure variations.

7. The device as recited in claim 1, wherein the second valve member is in the outlet chamber.

8. The device as recited in claim 1, wherein the second valve member is external to the outlet chamber.

9. The device as recited in claim 1, wherein the second valve member operates with a valve seat against which the second valve member is elastically compressed.

10. The device as recited in claim 1, wherein the second valve member comprises a ball valve structure.

11. The device as recited in claim 1, wherein the second valve member includes:
  a valve seat;
  a spring; and
  a ball elastically pressed against the valve seat by the spring and moveable away from the valve seat by a predetermined pressure.

12. The device as recited in claim 1, further including a bacterial particulate filter for filtering particulate matter from the infusion medium.

13. The device as recited in claim 1, wherein the piston is moveable in the axial direction of the channel between a retracted position and a forward position, wherein the first valve member is located in the closed position when the piston is in the retracted position and wherein the first valve member is moved to the opened position when the piston is moved to the forward position.

14. The device as recited in claim 1, wherein the piston is moveable in the axial direction of the piston channel between a retracted position and a forward position such that, upon the piston being in the retracted position, a volume is defined between the piston and the first valve member for receiving infusion medium through the piston channel under positive pressure and, upon the piston thereafter being moved toward the forward position, the volume between the piston and the first valve member decreases to increase infusion medium pressure within the volume, force the first valve member to the opened position and discharge infusion medium into the outlet chamber.

15. The device as recited in claim 1, further including:
a valve spring for urging the first valve member in the closed position;
wherein the first valve member and valve spring are located within the outlet chamber.

16. The device as recited in claim 1, wherein the second valve member comprises a valve member that is in a closed position to inhibit fluid flow when pressure within the outlet chamber exceeds a predefined level.

17. The device as recited in claim 1, wherein the reservoir provides a first positive fluid pressure to fluid in the outlet chamber upon the reservoir containing infusion medium under positive pressure and wherein the second valve member comprises a valve member that is in a closed position to inhibit fluid flow when pressure within the outlet chamber is at or below the first positive fluid pressure.

18. The device as recited in claim 1, wherein the reservoir provides a first positive fluid pressure to fluid in the outlet chamber upon the reservoir containing infusion medium under positive pressure and wherein the second valve member comprises a valve member that is in a closed position to inhibit fluid flow when pressure within the outlet chamber is at or below the first positive fluid pressure and is in an open position to allow fluid flow when pressure within the outlet chamber is greater than the first positive fluid pressure.

19. An infusion device for delivery of infusion medium comprising:
a reservoir for containing infusion medium under positive pressure;
a drive device having:
an inlet for receiving infusion medium under positive pressure;
at least one coil capable of being electrically activated to provide an electromagnetic field, the at least one coil surrounding an axial piston channel that provides a passage for communication of infusion medium received by the inlet;
an armature disposed adjacent the coil, on one side of the axial piston channel and moveable in a first direction relative to the coil, in response to the electromagnetic field produced by an activation of the coil;
a piston located within the piston channel and moveable axially within the channel in the first direction, in response to movement of the armature;
an outlet chamber disposed adjacent the coil, on the opposite side of the piston channel relative to the armature for receiving infusion medium from the piston channel under positive pressure, upon movement of the piston in the first direction;
an outlet in flow communication with the outlet chamber, for discharging infusion medium from the outlet chamber;
a first valve member positioned downstream of the piston channel in a flow path of infusion medium, said first valve member moveable between opened and closed positions to selectively open and close one end of the piston channel to the outlet chamber, said one end of the piston channel closed to the outlet chamber when the first valve member is in the closed position; and
a second valve member in fluid communication with the first valve member and positioned downstream of the first valve member in the flow path of infusion medium, the second valve member being moveable between opened and closed positions;
wherein the first valve member is configured such that the first valve member is in the opened position at least when infusion medium begins to be discharged from the outlet chamber.

20. The device as recited in claim 19, wherein the second valve member comprises a valve member that is in a closed position to inhibit fluid flow when pressure within the outlet chamber exceeds a predefined level.

21. The device as recited in claim 19, wherein the reservoir provides a first positive fluid pressure to fluid in the outlet chamber upon the reservoir containing infusion medium under positive pressure and wherein the second valve member comprises a valve member that is in a closed position to inhibit fluid flow when pressure within the outlet chamber is at or below the first positive fluid pressure.

22. The device as recited in claim 19, wherein the reservoir provides a first positive fluid pressure to fluid in the outlet chamber upon the reservoir containing infusion medium under positive pressure and wherein the second valve member comprises a valve member that is in a closed position to inhibit fluid flow when pressure within the outlet chamber is at or below the first positive fluid pressure and is in an open position to allow fluid flow when pressure within the outlet chamber is greater than the first positive fluid pressure.

23. An infusion device for delivering infusion medium, the device comprising:
a housing having an outlet through which infusion medium may be discharged;
a positive pressure reservoir disposed within the housing, for containing a volume of infusion medium under positive pressure;
a control circuit for providing drive control signals;
a drive mechanism disposed within the housing, for metering infusion medium out the outlet, in response to drive control signals from the control circuit; and
a power source disposed within the housing, for providing power to the control circuit and drive mechanism;
wherein the drive mechanism comprises:
an inlet for receiving infusion medium from the reservoir under positive pressure;
at least one coil capable of being electrically activated to provide an electromagnetic field in response to a signal from the control circuit, the at least one coil surrounding an axial piston channel that provides a passage for communication of infusion medium received by the inlet;
an armature disposed adjacent the coil, on one side of the axial channel and moveable in a first direction relative to the coil, in response to the electromagnetic field produced by an activation of the coil;
a piston located within the piston channel of the coil and moveable axially within the channel in the first direction, in response to movement of the armature;
an outlet chamber disposed adjacent the coil, on the opposite side of the piston channel relative to the armature for receiving infusion medium from the piston channel, upon movement of the piston in the first direction;
an outlet port in flow communication with the outlet chamber and the housing outlet, for discharging infusion medium from the outlet chamber, through the housing outlet;
a first valve member positioned downstream of the piston channel in a flow path of infusion medium, said first valve member moveable between opened and closed positions to selectively open and close one end of the piston channel to the outlet chamber, said one end of the piston channel closed to the outlet chamber when the first valve member is in the closed position; and a second valve member in fluid communication with the first valve member and positioned downstream of the first valve member in the flow path of infusion medium, the second valve member being moveable between opened and closed positions; and wherein the first valve member is configured such that the first valve member is in the opened position at least when infusion medium begins to be discharged from the outlet chamber.

24. The device as recited in claim 23, wherein the second valve member comprises a valve member that is in a closed position to inhibit fluid flow when pressure within the outlet chamber exceeds a predefined level.

25. The device as recited in claim 23, wherein the reservoir provides a first positive fluid pressure to fluid in the outlet chamber upon the reservoir containing infusion medium under positive pressure and wherein the second valve member comprises a valve member that is in a closed position to inhibit fluid flow when pressure within the outlet chamber is at or below the first positive fluid pressure.

26. The device as recited in claim 23, wherein the reservoir provides a first positive fluid pressure to fluid in the outlet chamber upon the reservoir containing infusion medium under positive pressure and wherein the second valve member comprises a valve member that is in a closed position to inhibit fluid flow when pressure within the outlet chamber is at or below the first positive fluid pressure and is in an open position to allow fluid flow when pressure within the outlet chamber is greater than the first positive fluid pressure.

* * * * *